United States Patent [19]
Lemmon et al.

[11] Patent Number: 6,054,280
[45] Date of Patent: Apr. 25, 2000

[54] METHODS FOR DIAGNOSIS AND TREATMENT OF PH DOMAIN SIGNAL TRANSDUCTION DISORDERS

[76] Inventors: Mark A. Lemmon; Kathryn M. Ferguson, both of 45 D Dora St., Stamford, Conn. 06904; Paul B. Sigler, 20 Edgehill Rd., New Haven, Conn. 06511; Joseph Schlessinger, 37 Washington Square, New York, N.Y. 10011

[21] Appl. No.: 08/407,165

[22] Filed: Mar. 20, 1995

[51] Int. Cl.⁷ .................................................. G01N 33/53
[52] U.S. Cl. .......................... 435/7.1; 435/183; 435/194; 436/501
[58] Field of Search ...................... 424/9.1, 9.2; 436/501; 435/183, 7.1, 194

[56] References Cited

PUBLICATIONS

Cifuentes et al., J. Biol Chem., vol. 269: 1945–1948, Jan. 1994.
Cifuentes et al., J. Biol. Chem., vol. 268: 11586–11593, Jun. 1993.
Shimohama et al., Neuroscience Letters, vol. 162: 183–186, May 1993.
Lee et al., Current Opinion in Cell Biology, vol. 7: 183–189, Feb. 1995.
Kato et al., J. Biol. Chem., 267:6483–6487, May 1992.
Harlan et al. Nature vol. 371:168–170, Sep. 1994.
Frech, "High Affinity Binding of Inositol Phosphates and Phosphoinositides to the Pleckstrin Homology Domain of RAC/Protein Kinase B and Their Influence on Kinase Activity," *J. Biological Chemistry* 272(13):8474–8481 (1997).
Pitcher, "Pleckstrin Homology Domain–mediated Membrane Association and Activation of the β–Adrenergic Receptor Kinase Requires Coordinate Interaction with Gβγ Subunits and Lipid," *J. Biological Chemistry* 270(20):11707–11710 (1995).
Yao, "Interactions Between Protein Kinase C and Pleckstrin Homology Domains," *J. Biological Chemistry*, 272(20):13033–13039 (1997).

*Primary Examiner*—Christina Y. Chan
*Assistant Examiner*—Patrick Nolan
*Attorney, Agent, or Firm*—Lyon & Lyon LLP

[57] ABSTRACT

Methods for treatment, diagnosis, and screening are provided for diseases or conditions characterized by an abnormality in a signal transduction disorder. The signal transduction pathway involves an interaction between a PH domain and a PH domain binding partner.

20 Claims, 6 Drawing Sheets

METHODS FOR DIAGNOSIS AND TREATMENT OF PH DOMAIN SIGNAL TRANSDUCTION DISORDERS

FIELD OF THE INVENTION

The present invention relates to products and methods useful for the diagnosis and treatment of various PH domain related diseases and conditions associated with abnormal cellular signal transduction pathways.

BACKGROUND OF THE INVENTION

None of the following is admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of tyrosine residues on proteins. The phosphorylation state of a protein is modified through the reciprocal actions of tyrosine kinases (TKs) and tyrosine phosphatases (TPs).

Receptor tyrosine kinases (RTKs) belong to a family of transmembrane proteins and have been implicated in cellular signaling pathways. The predominant biological activity of some RTKs is the stimulation of cell growth and proliferation, while other RTKs are involved in arresting growth and promoting differentiation. In some instances, a single tyrosine kinase can inhibit, or stimulate, cell proliferation depending on the cellular environment in which it is expressed.

RTKs are composed of at least three domains: an extracellular ligand binding domain, a transmembrane domain and a cytoplasmic catalytic domain that can phosphorylate tyrosine residues. Ligand binding to membrane-bound receptors induces the formation of receptor dimers and allosteric changes that activate the intracellular kinase domains and result in the self-phosphorylation (autophosphorylation and/or transphosphorylation) of the receptor on tyrosine residues. Their intrinsic tyrosine kinase is activated upon ligand binding, thereby initiating a complex signal transduction pathway that begins with receptor autophosphorylation and culminates in the tyrosine phosphorylation of a variety of cellular substrates and ultimately in the initiation of nuclear events necessary for the overall cell response. Individual phosphotyrosine residues of the cytoplasmic domains of receptors may serve as specific binding sites that interact with a host of cytoplasmic signaling molecules, thereby activating various signal transduction pathways.

The intracellular, cytoplasmic, non-receptor protein tyrosine kinases do not contain a hydrophobic transmembrane domain or an extracellular domain and share non-catalytic domains in addition to sharing their catalytic kinase domains. Such non-catalytic domains include the SH2 domains (SRC homology domain 2) and SH3 domains (SRC homology domain 3). The non-catalytic domains are thought to be important in the regulation of protein-protein interactions during signal transduction.

A central feature of signal transduction (for reviews, see Posada and Cooper, *Mol. Biol. Cell* 3:583–392, 1992; Hardie, *Symp. Soc. Exp. Biol.* 44:241–255, 1990), is the reversible phosphorylation of certain proteins. Receptor phosphorylation stimulates a physical association of the activated receptor with target molecules. Some of the target molecules such as phospholipase Cγ are in turn phosphorylated and activated. Such phosphorylation transmits a signal to the cytoplasm. Other target molecules are not phosphorylated, but assist in signal transmission by acting as adapter molecules for secondary signal transducer proteins. For example, receptor phosphorylation and the subsequent allosteric changes in the receptor recruit the Grb-2/SOS complex to the catalytic domain of the receptor where its proximity to the membrane allows it to activate ras.

The secondary signal transducer molecules generated by activated receptors result in a signal cascade that regulates cell functions such as cell division or differentiation. Reviews describing intracellular signal transduction include Aaronson, *Science*, 254:1146–1153, 1991; Schlessinger, *Trends Biochem. Sci.*, 13:443–447, 1988; and Ullrich and Schlessinger, *Cell*, 61:203–212, 1990.

The importance of modular binding domains in regulating interactions between signaling modules, as well as their activity, is well established. The pleckstrin homology (PH) domain has been proposed to represent such a module. It contains around 120 amino acids, and was identified as a region of sequence homology, shared with pleckstrin, that appeared in a large number of proteins known to be involved in intracellular signaling.

Several studies have suggested that PH domains, especially that of the β-adrenergic receptor kinase (βARK), bind the βγ-subunits of heterotrimeric G-proteins ($G_{\beta\gamma}$). A related suggestion is that PH domains recognize the β-transducin or WD-40 repeat, found in $G_\beta$ as well as in such proteins as RACK1, a receptor for activated protein kinase C (PKC). It has also been reported that the PH domain of the non-receptor tyrosine kinase Btk interacts directly with PKC.

PH domain ligands of a different nature have also been suggested. Yoon H. S. et al., *Nature* 369, 672–675, 1994 argued that the N-terminal PH domain of pleckstrin bore topological resemblance to retinol binding protein (RBP), and that it might bind a similarly hydrophobic ligand. However, retinol binds to a large cavity in the hydrophobic core of RBP, and there is no such cavity in the hydrophobic core of PH domains.

The amino-terminal region of phospholipase C-$\delta_1$ (PLC-$\delta_1$), which contains a PH domain is essential for high-affinity binding of the enzyme to lipid vesicles containing $PIP_2$. Proteolytic removal of the PLC-$\delta_1$ amino-terminal domain abolishes high affinity $PIP_2$ binding by the enzyme, although the fragments retain catalytic activity. In common with other phospholipases, intact PLC-$\delta_1$ hydrolyzes micellar or bilayer aggregates of its substrate more effectively than it does substrate monomers. It has been suggested that the amino-terminal region of PLC-$\delta_1$ represents a noncatalytic substrate binding site that serves to absorb the enzyme to a membrane containing $PIP_2$. Cifuentes, M. E. et al., *J. Biol. Chem.* 268, 11586–11593, 1993. Under these conditions, the catalytic moiety could hydrolyze substrate processively, while remaining associated with the membrane; "scooting" along the interface as described for secretory phospholipase $A_2$ ($sPLA_2$). Ramirez, F., and Jain, M. K., *Proteins, Structure, Function and Genetics*, 9:229–239, 1991.

D-myo-inositol 1,4,5-trisphosphate (I(145)$P_3$), the head-group product of $PIP_2$ hydrolysis by PLC, also binds to PLC-$\delta_1$, and inhibits its high-affinity binding to $PIP_2$-containing vesicles. I(145)$P_3$ inhibits PLC-$\delta_1$ activity in an apparently noncompetitive fashion. Removal of the amino-terminal portion of PLC-$\delta_1$, in addition to preventing high-affinity binding to $PIP_2$, abolishes the effects of I(145)$P_3$, indicating that $PIP_2$ and I(145)$P_3$ bind to the same site.

Harlan, J. E. et al., *Nature* 371, 168–170, 1994, have reported that several PH domains, including two from pleckstrin, as well as those from RasGAP, Tsk and βARK, can bind to vesicles containing phosphatidylinositol-(4,5)-bisphosphate (PIP$_2$). The measured K$_D$ for binding of the N-terminal pleckstrin PH domain to PIP$_2$ in detergent was around 30 μM.

SUMMARY OF THE INVENTION

The present invention relates to methods for diagnosis and treatment of a disorder, preferably a disorder characterized by an abnormality in a signal transduction pathway, wherein the signal transduction pathway involves the interaction between a PH domain and a PH domain binding partner. We have determined that disruption or promotion of the interaction between a PH domain and PH domain binding partner is useful in therapeutic procedures.

Thus, we have determined that a PH domain is involved in molecular interactions of therapeutic importance. This interaction is associated with the basic signalling function of proteins associated with various diseases or conditions. PH domain proteins are involved in various signal transduction pathways and thus the present invention provides several agents and methods useful for diagnosing, treating, and preventing various diseases or conditions associated with abnormalities in these pathways.

The present invention is based in part on the suprising discovery that the isolated PH domain of PLC-δ$_1$ interacts specifically, and with high affinity, with both PIP$_2$ and I(145)P$_3$. The PH domain is therefore likely to represent the portion of PLC-δ$_1$ responsible for the negative regulation of interfacial activation that has been reported for the whole enzyme. This is the first demonstration of a specific high affinity ligand for a PH domain, and strongly suggests a functional role for PH domains in the regulation of PLC isoforms. A general function in regulated membrane association is thus anticipated for other PH domains which can be shown to bind additional membrane components in a similar manner.

Thus, in a first aspect, the invention features a method for treating a patient having a disease or condition characterized by an abnormality in a signal transduction pathway, wherein the signal transduction pathway involves the interaction between a PH domain and a PH domain binding partner. The disorder may also be characterized by an abnormal level of interaction between a PH domain and a PH domain binding partner. The method includes disrupting or promoting that interaction (or signal) in vivo. The method also involves inhibiting or promoting the activity of the complex formed between PH domain and a PH domain binding partner.

By "disease or condition" is meant a state which is recognized as abnormal by members of the medical community. The disease or condition may be characterized by an abnormality in one or more signal transduction pathways in a cell wherein one of the components of the signal transduction pathway is a PH domain. As the PH domain is found in over 70 proteins which perform a wide variety of functions, the diseases or conditions encompassed by the present invention is far reaching. Examples of diseases or conditions to be treated or diagnosed by the present invention include neuroproliferative disorders, cancers, and hyperproliferative disorders such as psoriasis and neurofibromatosis. These and other diseases or conditions are often characterized by one or more of the following symptoms: tumors, astasia, aphasia, paralysis, paresea, and paralagies. In preferred embodiments the disease in human mammary cancer or hypertension. A high percentage of primary human mammary carcinomas concomitantly display increased levels of PLC-γ1 and studies with spontaneously hypertensive rats have suggested the abnormal activation of PLC-δ1 may be one of the main causes of hypertension in these rats which results from point mutations in the X and Y regions. Arteag, C. L., et al., *PNAS* 88:10435–10439, 1991; Kato, H., et al., *J. Biol. Chem.* 267:6483–6487, 1992; and Yagisawa, H., et al., *J. Hypertens.* 9:997–1004, 1991, all of which are incorporated herein by reference in their entirety including any drawings.

By "abnormality" is meant a level which is statistically different from the level observed in organisms not suffering from such a disease or condition and may be characterized as either an excess amount, intensity or duration of signal or a deficient amount, intensity or duration of signal. The abnormality in signal transduction may be realized as an abnormality in cell function, viability or differentiation state. We have determined that such abnormal interaction in a pathway can be alleviated by action at the PH domain-binding partner interaction site in the pathway. An abnormal interaction level may also either be greater or less than the normal level and may impair the normal performance or function of the organism. Thus, it is also possible to screen for agents that will be useful for treating a disease or condition, characterized by an abnormality in the signal transduction pathway, by testing compounds for their ability to affect the interaction between a PH domain and a PH domain binding partner, since the complex formed by such interaction is part of the signal transduction pathway. However, the disease or condition may be characterized by an abnormality in the signal transduction pathway even if the level of interaction between the PH domain and a PH domain binding partner is normal.

By "interact" is meant any physical association between proteins, other molecules such as lipids, carbohydrates, nucleotides and other cell metabolites, whether covalent or non-covalent. Thus, examples of interaction would include protein-protein interactions, protein-lipid interactions, lipid-lipid interactions, and others. Examples of non-covalent bonds include electrostatic bonds, hydrogen bonds, and Van der Waals bonds. Stryer, *Biochemistry*, 1988, pages 7–8. Furthermore, the interactions between proteins and other cellular molecules may either be direct or indirect. Another example of an indirect interaction is the independent production, stimulation, or inhibition of both PH domain and a PH domain binding partner by a regulatory agent. Depending upon the type of interaction present, various methods may be used to measure the level of interaction. For example, the strengths of covalent bonds are often measured in terms of the energy required to break a certain number of bonds (i.e., kcal/mol) Non-covalent interactions are often described as above, and also in terms of the distance between the interacting molecules. Indirect interactions may be described in a number of ways, including the number of intermediary agents involved, or the degree of control exercised over the PH domain relative to the control exercised over the PH domain binding partner.

By "PH domain" is meant a polypeptide having homology to an approximately 100 amino acid region of pleckstrin. The total number of proposed PH domains now exceeds 70. Recent structural studies have demonstrated that PH domains are distinct structural modules. The fold is best described as a seven-stranded β sandwich of two orthogonal b sheets that is closed at one corner by a C-terminal α helix. A polarization of the domain is evident, with the three most variable loops forming a positively charged surface at the corner of the sandwich opposite from that closed off by the α helix. Ferguson, K. M. et al., *Cell*, 79, 199–209, 1994, incorporated herein by reference in its entirety, including any drawings. Examples of various PH domains are provided in Musacchio, A., et al., *TIBS,* 18:343–348, 1993 and Gibson, T. J., et al., *TIBS,* 19:349–353, 1994, both of which are incorporated herein by reference in their entirety, including any drawings. Other PH domains may be identified using the sequence alignment techniques and three dimensional structure comparisions described in those publications. Preferred PH domains include those in serine/threonine as well as tyrosine kinases; regulators of small GTP-binding proteins; cytoskeletal proteins; and putative signaling adapter molecules. Especially preferred PH domains are those from dynamin, proteins involved in cellular membrane transport and phospholipase C isoforms. The cloning and sequence of multiple forms of phospholipase C is described in Suh, et al., *Cell,* 54:161–169, 1988, incorporated herein by reference in its entirety, including any drawings.

By "PH domain binding partner" is meant an amino acid sequence or any other cellular molecule that interacts with or binds a PH domain. The term includes ligands and/or substrates for the PH domains, as well as PH domain agonists or antagonists. In preferred embodiments the interaction is specific, i.e., the binding partner does not interact, or interacts to a lesser extent, with non-PH domains. The $K_D$ for the interaction between the PH domain and the binding partner is preferably less than 10 $\mu$M, more preferably 1,000 nM, most preferably 500 nM. Especially preferred binding partners are $PIP_2$ and $I(145)P_3$ and negatively charged ligands. In preferred embodiments the PH domain or binding partner may be provided as part of a protein, alone in isolation from the remainder of the amino acid sequence of the protein, or contained in a lipid vessicle, or as a freely soluble small molecule. The interaction between the PH domain and the PH domain binding partner may be promoted or disrupted in a variety of ways, including altering or affecting a molecule that encodes an enzyme responsible for synthesis of PH domain or binding partner (e.g., a small molecule ligand).

By "disrupt" is meant that the interaction between the PH domain and a PH domain binding partner is reduced either by preventing production of the PH domain, or by preventing expression of the PH domain binding partner, or by specifically preventing interaction of the naturally synthesized proteins having these domains or by interfering with the interaction of the proteins.

By "promote" is meant that the interaction between a PH domain and a PH domain binding partner is increased either by increasing production of a PH domain, or by increasing expression of a PH domain binding partner, or by promoting interaction of the PH domain and a PH domain binding partner or by prolonging the duration of the interaction. Many bivalent or polyvalent linking agents are useful in coupling polypeptides and other cellular molecules, such as an antibody, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See Killen and Lindstrom 1984, *J. Immunol.* 133:1335–2549; Jansen, F. K., et al. 1982, *Immunological Rev.* 62:185–216; and Vitetta et al., supra).

By "signal transduction pathway" is meant the sequence of events that involves the transmission of a message from an extracellular protein to the cytoplasm through a cell membrane. The signal ultimately will cause the cell to perform a particular function, for example, to uncontrollably proliferate and therefore cause cancer. Various mechanisms for the signal transduction pathway (Fry et al., *Protein Science,* 2:1785–1797, 1993) provide possible methods for measuring the amount or intensity of a given signal. Depending upon the particular disease associated with the abnormality in a signal transduction pathway, various symptoms may be detected. Those skilled in the art recognize those symptoms that are associated with the various diseases described herein. Furthermore, since some adapter molecules recruit secondary signal transducer proteins towards the membrane, one measure of signal transduction is the concentration and localization of various proteins and complexes. In addition, conformational changes that are involved in the transmission of a signal may be observed using circular dichroism and fluorescence studies.

In a related aspect the invention features a method for screening for an agent useful for treatment of such a disease or condition by assaying potential agents for the ability to disrupt or promote that interaction. The screening may also involve assaying potential agents for the ability to remove or reduce the effect of an abnormality in a signal transduction pathway, wherein the signal transduction pathway contains a PH domain and a PH domain binding partner.

By "screening" is meant investigating for the presence or absence of a property, preferably in an organism. The process may include measuring or detecting various properties, including the level of signal transduction and the level of interaction between a PH domain and a PH domain binding partner. Useful agents for treatment of such diseases can be identified by standard screening protocols in which measurement of such interaction is determined. For example, such an agent may be a peptide which either comprises, consists of, or consists essentially of a PH domain or binding partner, a molecule that contains a PH domain, or a fragment of any of the above.

By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In preferred embodiments the screening involves looking for agonists or antagonists of a protein of interest, for example a PH domain or a PH domain binding partner. The term agonist refers to agents that bind the protein and that maintain the activity of the protein to which they bind. An antagonist competes with the natural ligand for binding the protein, but does not maintain the activity of the protein to which it binds.

Another aspect of the invention features a method for diagnosis of such a disease or condition. The method includes detecting the level of interaction between a PH domain and a PH domain binding partner.

By "diagnosis" is meant any method of identifying a symptom normally associated with a given disease or condition. Thus, an initial diagnosis may be conclusively established as correct by the use of additional confirmatory evidence such as the presence of other symptoms. Current classification of various diseases and conditions is constantly changing as more is learned about the mechanisms causing the diseases or conditions. Thus, the detection of an important symptom, such as the detection of an abnormal level of interaction between the PH domains and binding partners may form the basis to define and diagnose a newly named disease or condition. For example, conventional neurological diseases are classified according to the presence of a particular set of symptoms. However, a subset of these symptoms may both be associated with an abnormality in a particular signalling pathway, such as the $ras^{21}$ pathway and in the future these diseases may be reclassified as $ras^{21}$ pathway diseases regardless of the particular symptoms observed.

In other preferred embodiments the agent is therapeutically effective and has an $EC_{50}$ or $IC_{50}$ as described below. An $EC_{50}$ or $IC_{50}$ of less than or equal to 5 $\mu$M is preferable, and even more preferably less than or equal to 1 $\mu$M, 100 nmolar, 10 nmolar, or 1 nmolar. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness. In addition, the molecule may have an $EC_{50}$ or $IC_{50}$ less than or equal to 5 $\mu$M at one or more, but not all cells chosen from the group consisting of colon cancer cell, parathyroid cell, bone osteoclast, juxtaglomerular kidney cell, proximal tubule kidney cell, distal tubule kidney cell, cell of the thick ascending limb of Henle's loop and/or collecting duct, central nervous system cell, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition. Generally, a therapeutically effective amount is between about 1 nmole and 1 $\mu$mole of the molecule, depending on its $EC_{50}$ or $IC_{50}$ and on the age and size of the patient, and the disease associated with the patient.

In another aspect the invention features a composition comprising a therapeutically effective amount of a mimetic of a specific PH domain binding partner and a pharmaceutically acceptable carrier or diluent. Methods of designing and producing such mimetics are described herein. In preferred embodiments, the binding partner has submicromolar affinity for a PH domain. The mimetic may be a small molecule (MW preferably less than 10,000, more preferably less than 1,000, most preferably less than 500) or peptide (less than 30 amino acids preferably, less than 20 more preferably, less than 10 most preferably) designed to bind to the PH domain.

In another aspect the invention features a method of using a specific high affinity PH domain ligand to design small molecule mimetics, agonists, or antagonists comprising determining the amino acid sequence and/or three dimensional structure of a binding site and providing a small molecule or peptide capable of binding said binding site. Those skilled in the art given the present disclosure of the first specific high affinity PH domain ligand will be able to produce small molecules or peptides that mimic the effect of the ligand and that are capable of easily entering the cell. Once the ligand is identified, fragments therof can be assayed for their ability to bind the PH domain, and the strength of the interaction may be optimized by making amino acid deletions, additions or substitutions or by adding, deleting or substituting a functional group on a small molecule. The additions, deletions, or modifications to the amino acid sequence of the ligand (or alterations in the small molecule) can be made at random or may be based on knowledge of the size, shape, and three-dimensional structure of the binding region.

In other aspects, products and methods useful for PH domain related gene therapy and gene transfer techniques are provided. Thus, in preferred embodiments the invention provides cell lines and "knock-out" mice for performing such techniques. The choice of transfected lineages, vectors, and targets may all be confirmed, for example, in a mouse animal model. In preferred embodiments the disease or condition to be treated by gene therapy is or is not the human immunodeficiency, X-linked agammaglogulinemia.

In particular, the invention provides a vector comprising nucleic acid encoding a human or mouse PH domain, ligand, enzyme responsible for ligand synthesis, or ligand mimetic, the vector being adapted to cause expression of the PH domain, ligand, enzyme responsible for ligand synthesis, or ligand mimetic. Expression of the human or mouse PH domain or binding partner may result in the production of functional human or mouse PH domain or binding partner. The vector may comprise a retroviral vector. In addition, the invention provides a vector comprising nucleic acid encoding a PH domain or binding partner the vector being adapted to cause expression of the PH domain or binding partner only in specific tissue.

Also provided is a transfected cell line containing a vector comprising nucleic acid encoding a human or mouse PH domain or binding partner. PH domain or binding partner may be expressed as a secreted protein. A transformed cell line containing a vector comprising nucleic acid encoding a human or mouse PH domain or binding partner is also encompassed by the present invention. Again, the human or mouse PH domain or binding partner may be expressed as a secreted protein.

A transgenic non-human animal containing a PH domain or binding partner is also provided. The transgenic animal may be a mammal, in particular a mouse. Also provided is a method for introducing a continuous supply of PH domain or binding partner into an animal or tissue culture, comprising the step of administering an effective amount of a vector described above to an animal or into the tissue culture. The step of administration to an animal may comprise injection into a skeletal muscle of the animal.

In addition, a method of gene replacement, comprising the step of administering an effective amount of a vector described above to an animal, wherein the PH domain or binding partner nucleic acid sequence will correct a genetic condition characterized by a defective or nonexistent PH domain or binding partner is provided.

Further provided is a method of screening compounds for their pharmacological effects on biological activities such as tyrosine phosphorylation comprising the steps of administering a compound to a transgenic animal expressing a PH domain or binding partner and measuring the activity in the transgenic animals. Any activity of protein that contains a PH domain may be screened, including GTPase activity, and phospholipase C activity.

The invention also features a method of administering a nucleic acid sequence encoding a PH domain or binding partner to an animal comprising the steps of removing cells from the animal, transducing the cells with the PH domain or binding partner nucleic acid sequence, and reimplanting the transduced cells into the animal. The nucleic acid sequence may encode a human or mouse PH domain or binding partner.

Also featured is a method of administering a PH domain or binding partner nucleic acid sequence utilizing an in vivo approach comprising the steps of administering directly to an animal the PH domain or binding partner nucleic acid sequence selected from the group of methods of administration consisting of intravenous injection, intramuscular injection, or by catheterization and direct delivery of the PH domain or binding partner nucleic acid sequence via the blood vessels supplying a target organism. The PH domain or binding partner nucleic acid sequence may encode a human PH domain or binding partner and the animal to which the PH domain or binding partner is administered may be a human. The target organ can be selected from the group consisting of heart, skeletal muscle, adipose tissues, spleen, lung, brain, kidney, testis, adrenal or small intestine. The PH domain or binding partner nucleic acid sequence may be administered as naked DNA or may be contained in a viral vector, for example one selected from the group consisting of papovaviruses, adenovirus, vaccinia virus, adeno-associated virus, herpesviruses and retroviruses of avian, murine or human origin.

Featured herein is a method of administering a PH domain or binding partner nucleic acid sequence in a two-component system comprising the steps of administering a packaging cell, wherein the packaging cell produces a viral vector. The packaging cell can be administered to cells in vitro.

Also provided is a method of administering a PH domain or binding partner nucleic acid sequence comprising the step of administering a retroviral vector containing the PH domain or binding partner nucleic acid sequence, wherein a retroviral envelope glycoprotein is replaced with the G glycoprotein of vesicular stomatitis virus.

The invention also features a method of administering a PH domain or binding partner nucleic acid sequence comprising the step of administering to an animal an adenovirus vector, wherein an E1 region of the adenovirus vector is replaced with the PH domain, ligand, or ligand mimetic nucleic acid sequence and administering the adenovirus vector by a method of administration selected from the group consisting of intravenous injection, intramuscular injection, intraportal injection or intraarterial injection.

The summary of the invention described above is non-limiting and other features and advantages of the invention will be apparent from the following description of the preferred embodiments, and from the claims.

BRIEF DESCRIPTION OF THE DRAWINGS

FIG. 2 illustrates that $I(145)P_3$ binds to PLCδ-PH.

FIG. 4 shows binding of PLCδ-PH to $PIP_2$-containing lipid vesicles.

DESCRIPTION OF THE PREFERRED EMBODIMENTS

Figure 1:
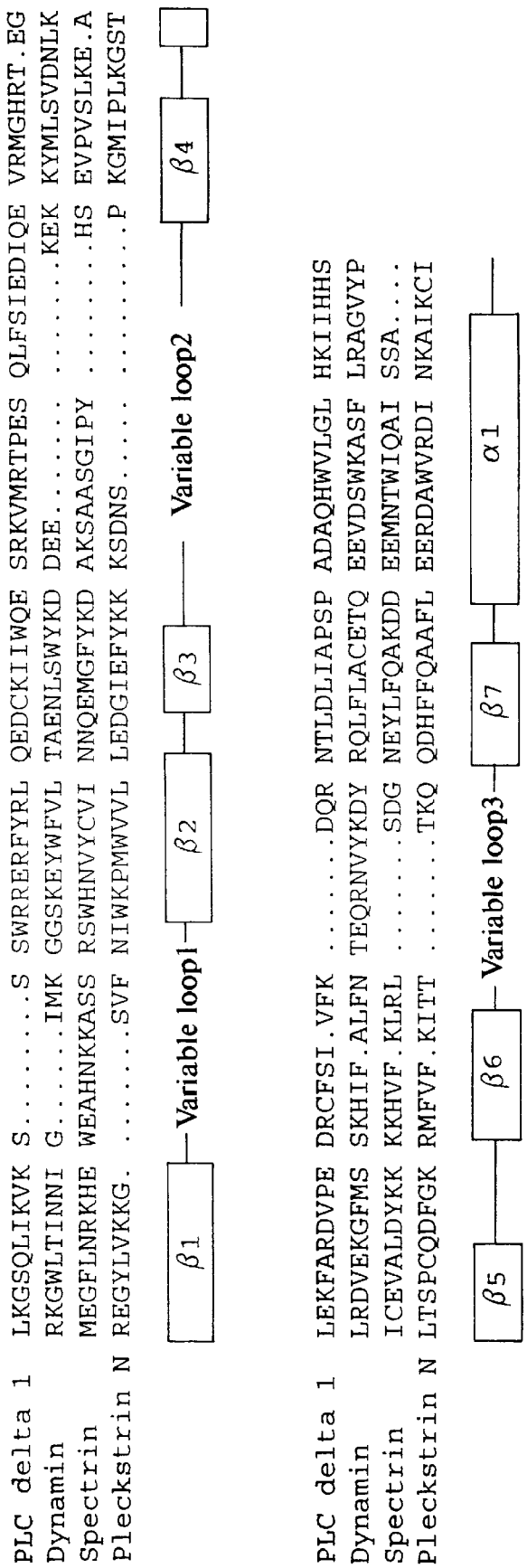
FIG. 1 shows a sequence alignment of PLCδ-PH domain with the three PH domains of known structure SEQ ID NO.s 1–4). Where there are two or more identical residues at a given position, they are blocked in black. Where there are two or more homologous residues at a given position, they are shaded in grey. The positions of secondary structural elements are also marked.

The present invention relates to methods for diagnosis and treatment of a disorder, preferably a disorder characterized by an abnormality in a signal transduction pathway, wherein the signal transduction pathway involves the interaction between a PH domain and a PH domain binding partner.

The invention is based in part on our suprising discovery that the isolated pleckstrin homology (PH) domain from rat phospholipase C-$\delta_1$ (PLC$\delta_1$) binds to D-myo-inositol (1,4,5) trisphosphate (I(145)P$_3$) with a K$_D$ of 200 nM. Binding is specific, in that any inositol polyphosphate with a different arrangement of phosphate groups does not bind or binds at least an order of magnitude weaker. The PH domains of dynamin and pleckstrin, by contrast, bind only very weakly to the inositol polyphosphates tested (K$_D \approx$ 100 $\mu$M).

Lipid vesicles containing phosphatidylinositol (4,5) bisphosphate (PIP$_2$) compete for I(145)P$_3$ binding to the PLC$\delta_1$ PH domain, and themselves bind with K$_D$=1 $\mu$M. I(145)P$_3$ is therefore likely to reduce the affinity of PLC-$\delta_1$ for PIP$_2$-containing membranes. Indeed, I(145)P$_3$ has been shown to have this effect upon the whole enzyme, and to inhibit PLC$\delta_1$ activity. Proteolytic removal of an N-terminal portion of PLC$\delta_1$ has also been shown to destroy this negative feedback mechanism.

The data presented here show that the PH domain alone of PLC-$\delta_1$ (PLC$\delta$PH) could be responsible for the PIP$_2$ binding by the enzyme that permits processive catalysis, and also confers the potential for regulation of this step. Since other PH domain-containing proteins are associated with membrane surfaces, and PH domains can bind to specific sites on membranes, this finding suggests a general role for PH domains.

The data presented here provide the first demonstration of a PH domain ligand that binds with both high affinity and a high degree of specificity. I(145)P$_3$, GPIP$_2$ and PIP$_2$ in vesicles all bind to PLC$\delta$-PH, via their common I(145)P$_3$ moiety, with submicromolar affinities. A number of other inositol phosphates also bind to PLC$\delta$-PH, but in each case the affinity is more than ten-fold less than that seen for I(145)P$_3$ (Table 2). None of the inositol polyphosphates studied bind with significant affinity to the other PH domains that we have tested.

The findings reported here for PLC$\delta$-PH suggest that the PH domain plays an important role in regulation of enzyme activity. Phospholipases act upon aggregated forms of their substrates (such as in lipid bilayers) more effectively than upon monomeric forms. PLC-$\delta_1$ is no exception in this, although the magnitude of the effect is considerably less than that seen for sPLA$_2$. In the case of sPLA$_2$, it is clear that high-affinity binding of the enzyme to the membrane interface is at least partly responsible for the increased rate of hydrolysis of vesicle-bound phospholipids. This permits a processive mode of catalysis, in which the enzyme can "scoot" across the surface of the vesicle, without having to dissociate and rebind.

PLC-$\delta_1$ similarly binds with high affinity to lipid vesicles containing its substrate, PIP$_2$ (Rebecchi, M. et al., *Biochemistry* 31, 12742–12747, 1992). Furthermore, as is seen with PLA$_2$ for its substrates, the apparent V$_{max}$ for hydrolysis by PLC-$\delta_1$ of PIP$_2$ in mixed lipid/detergent micelles increases (at constant PIP$_2$ concentration) with the lipid:detergent ratio. This is indicative of the existence of PIP$_2$ binding sites on PLC-$\delta_1$ in addition to that involved in catalysis. Similar observations have been reported for PLC-$\gamma_1$. Upon proteolytic removal of the amino-terminal portion of PLC-$\delta_1$, this behavior is lost, along with the high affinity of the enzyme for PIP$_2$-containing vesicles. The region that is removed includes the PH domain, which we have shown itself binds to PIP$_2$-containing vesicles with high affinity. Therefore, PLC$\delta$-PH represents the lipid binding site that is responsible, at least in part, for the enhanced ability of PLC-$\delta_1$ to hydrolyze bilayer-bound, rather than monomeric PIP$_2$.

Compared with the binding of sPLA$_2$ molecules to lipid bilayers, which appears to involve interaction with anionic phospholipids in general, PH domain-mediated absorption of PLC-$\delta_1$ is highly specific. This is consistent with the substrate requirements of the two enzymes. Indeed, head group-specific phospholipases would be expected to require a different mode of membrane absorption than those more promiscuous in their substrate requirements. The alternative would be absorption to membranes devoid of their substrate. In addition, such a specific mode of membrane absorption offers an additional means of regulation for the enzyme. I(145)P$_3$ produced by PLC-$\delta_1$ activity can inhibit its association with PIP$_2$-containing membranes in a specific manner. This is manifest in the behavior of I(145)P$_3$ as an inhibitor of PLC-$\delta_1$ activity. The PH domain, in binding both PIP$_2$ and I(145)P$_3$ provides this regulatory function.

Since both PLC-$\gamma$ and PLC-$\beta$ isoforms have also been argued to contain PH domains, the domains may play a similar regulatory role in these enzymes. Kinetic studies of PLC-$\gamma_1$ do indicate that there is likely to be a noncatalytic substrate binding site, as shown for PLC-$\delta_1$.

The results reported here for PLC-$\delta_1$ may be extended to other PH domains, although most PH domain-containing proteins are not involved in interfacial catalysis. However, all such proteins appear to have a functional requirement for membrane association. Therefore, a general role for PH domains might be in specific membrane association. Such specific association might be inhibited by some soluble compound. It is clear that the PH domain of $\beta_{65}$ spectrin does bind to specific sites in stripped bovine brain membranes. In addition, it has been reported that dynamin binds to phospholipid membranes in a Ca$^{2+}$-dependent manner.

I. Compositions

The present invention relates to removing or reducing an abnormality in a signal transduction pathway, wherein the signal transduction pathway contains a PH domain and a PH domain binding partner. The present invention also relates to compositions and methods for the treatment of disorders which involve modulating the activity and/or level of individual components, and relates to methods for the identification of agents for such treatments. Additionally, the present invention relates to methods and compositions for prognostic evaluation of such disorders.

Described herein are compositions and methods for the prevention, prognostic evaluation, and treatment of disorders in which a PH domain may be involved, in particular, cell proliferative disorders, especially cancer, in which a PH domain is involved.

First, methods and compositions for the treatment of such disorders are described. Such methods and compositions may include, but are not limited to the agents capable of decreasing or inhibiting the interaction between a PH domain and a PH domain binding partner and agents capable of inhibiting or decreasing the activity of such complexes, agents capable of modulating the activity and/or level of individual components of the proteins, and the use and administration of such agents.

Second, methods are described for the identification of such agents. These methods may include, for example, assays to identify agents capable of disrupting or inhibiting or promoting the interaction between components of the complexes (e.g., PH domain:binding partner complexes), and may also include paradigms and strategies for the rational design of drugs capable of disruption and/or inhibition and/or promotion of such complexes.

II. Binding Partner/Receptor Complexes

The complexes involved in the invention include a PH domain and a PH domain binding partner or derivatives thereof, as described below. Under standard physiological conditions, the components of such complexes are capable of forming stable, non-covalent attachments with one or more of the other complex components. Methods for the purification and production of such protein complexes, and of cells that exhibit such complexes are described below.

III. Disruption of Protein Complexes

Disruption of complexes (e.g., PH domain:binding partner complexes), for example by decreasing or inhibiting or promoting the interactions between component members of such a complex may have differing modulatory effects on the event involved, depending on the individual protein complex. "Disruption", as used here, is meant to refer not only to a physical separation of protein complex components, but also refers to a perturbation of the activity of the complexes, regardless of whether or not such complexes remain able, physically, to form. "Activity", as used here, refers to the function of the protein complex in the signal transduction cascade of the cell in which such a complex is formed, i.e., refers to the function of the complex in effecting or inhibiting a transduction of an extracellular signal into a cell. For example, the effect of complex disruption may augment, reduce, or block a signal normally transduced into the cell. Likewise, depending on the disorder involved, either augmentation, reduction, or blockage of a signal normally transduced into the cell will be desirable for the treatment of the disorder.

A disorder involving a complex may, for example, develop because the presence of such a complex brings about the aberrant inhibition of a normal signal transduction event. In such a case, the disruption of the complex would allow the restoration of the usual signal transduction event. Further, an aberrant complex may bring about an altered subcellular adapter protein localization, which may result in, for example, dysfunctional cellular events. An inhibition of the complex in this case would allow for restoration or maintenance of a normal cellular architecture. Still further, an agent or agents that cause(s) disruption of the complex may bring about the disruption of the interactions among other potential components of a complex.

Nucleotide sequences encoding peptide agents which are to be utilized intracellularly may be expressed in the cells of interest, using techniques which are well known to those of ordinary skill in the art. For example, expression vectors derived from viruses such as retroviruses, vaccinia virus, adenoviruses, adeno-associated virus, herpes viruses, or bovine papilloma virus, may be used for delivery and expression of such nucleotide sequences into the targeted cell population. Methods for the construction of such vectors are well known. See, for example, the techniques described in Maniatis et al., 1989, *Molecular Cloning: A Laboratory Manual*, Cold Spring Harbor Laboratory, N.Y. and in Ausubel et al., *Current Protocols in Molecular Biology*, Greene Publishing Associates and Wiley Interscience, New York, 1989. Complex-binding domains can be identified using, for example, techniques such as those described in Rotin et al. (Rotin et al., *EMBO J.* 11:559–567, 1992), Songyang et al. (Songyang et al., *Cell* 72:767–778, 1993), Felder et al., *Mol. Cell. Biol.* 13:1449–1455, 1993), Fantl et al. (*Cell* 69:413–422, 1992), and Domchek et al. (*Biochemistry* 31:9865–9870, 1992).

Alternatively, antibodies capable of interfering with complex formation may be produced as described below and administered for the treatment of disorders involving a component capable of forming a complex with another protein. For example, neutralizing antibodies which are capable of interfering with ligand binding may be administered using standard techniques. Alternatively, nucleotide sequences encoding single-chain antibodies may be expressed within the target cell population by utilizing, for example, techniques such as those described in Marasco et al. (Marasco et al., *Proc. Natl. Acad. Sci. USA* 90:7889–7893, 1993).

Agents which act intracellularly to interfere with the formation and/or activity of the protein complexes of the invention may also be small organic or inorganic compounds. A method for identifying these and other intracellular agents is described below.

IV. Antibodies to Complexes

Described herein are methods for the production of antibodies which are capable of specifically recognizing a complex or an epitope thereof, or of specifically recognizing an epitope on either of the components of the complex, especially those epitopes which would not be recognized by the antibody when the component is present separate and apart from the complex. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies may be used, for example, in the detection of a complex in a biological sample, or, alternatively, as a method for the inhibition of a complex formation, thus inhibiting the development of a disorder.

Polyclonal antibodies are heterogeneous populations of antibody molecules derived from the sera of animals immunized with an antigen, such as a complex, or an antigenic functional derivative thereof. For the production of polyclonal antibodies, various host animals may be immunized by injection with the complex including but not limited to rabbits, mice, rats, etc. Various adjuvants may be used to increase the immunological logical response, depending on the host species, including but not limited to Freund's (complete and incomplete), mineral gels such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

A monoclonal antibody, which is a substantially homogeneous population of antibodies to a particular antigen, may be obtained by any technique which provides for the production of antibody molecules by continuous cell lines in culture. These include, but are not limited to the hybridoma technique of Kohler and Milstein (*Nature* 256:495–497, 1975) and U.S. Pat. No. 4,376,110), the human B-cell hybridoma technique (Kosbor et al., *Immunology Today* 4:72, 1983; Cole et al., *Proc. Natl. Acad. Sci. USA* 80:2026–2030, 1983), and the EBV-hybridoma technique (Cole et al., *Monoclonal Antibodies And Cancer Therapy*, Alan R. Liss, Inc., 1985, pp. 77–96). Such antibodies may be of any immunoglobulin class including IγG, IγM, IγE, IγA, IγD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Natl. Acad. Sci.*, 81:6851–6855, 1984; Neuberger et al., *Nature,* 312:604–608, 1984; Takeda et al., *Nature,* 314:452–454, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, Science 242:423–426, 1988; Huston et al., Proc. Natl. Acad. Sci. USA 85:5879–5883, 1988; and Ward et al., Nature 334:544–546, 1989) can be adapted to produce complex-specific single chain antibodies. Single chain antibodies are formed by linking the heavy and light chain fragment of the Fv region via an amino acid bridge, resulting in a single chain polypeptide.

Antibody fragments which contain specific binding sites of a complex may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity to the PH domain:binding partner complex.

One or more components of a protein complex may be present at a higher than normal cellular level (i.e., higher than the concentration known to usually be present in the cell type exhibiting the protein complex of interest) and/or may exhibit an abnormally increased level of cellular activity (i.e., greater than the activity known to usually be present in the cell type exhibiting the protein complex of interest).

For example, the gene encoding a protein complex component may begin to be overexpressed, or may be amplified (i.e., its gene copy number may be increased) in certain cells, leading to an increased number of component molecules within these cells. Additionally, a gene encoding a protein complex component may begin to express a modified protein product that exhibits a greater than normal level of activity. "Activity", here, refers to the normal cellular function of the component, either enzymatic or structural whose function may include, for example, bringing two or more cellular molecules into the appropriate proximity.

Such an increase in the cellular level and/or activity of a protein complex may lead to the development of a disorder. Treatment of such disorders may, therefore, be effectuated by the administration of agents which decrease the cellular level and/or the activity of the overexpressed and/or overactive PH domain:binding partner complex component.

Techniques for decreasing the cellular level and/or the activity of one or more of the protein complex components of interest may include, but are not limited to antisense or ribozyme approaches, and/or gene therapy approaches, each of which is well known to those of skill in the art.

V. Antisense and Ribozyme Approaches to Provide or Disrupt the Complexes of the Present Invention Included in the scope of the invention are oligoribonucleotides, including antisense RNA and DNA molecules and ribozymes that function to inhibit translation of one or more components of a protein complex. Anti-sense RNA and DNA molecules act to directly block the translation of mRNA by binding to targeted mRNA and preventing protein translation. With respect to antisense DNA, oligodeoxyribonucleotides derived from the translation initiation site, e.g., between −10 and +10 regions of the relevant nucleotide sequence, are preferred.

Ribozymes are enzymatic RNA molecules capable of catalyzing the specific cleavage of RNA. The mechanism of ribozyme action involves sequence specific interaction of the ribozyme molecule to complementary target RNA, followed by a endonucleolytic cleavage. Within the scope of the invention are engineered hammerhead or other motif ribozyme molecules that specifically and efficiently catalyze endonucleolytic cleavage of RNA sequences encoding protein complex components.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays. See, Draper PCT WO 93/23569.

Both anti-sense RNA and DNA molecules and ribozymes of the invention may be prepared by any method known in the art for the synthesis of RNA molecules. See, Draper, id. hereby incorporated by reference herein. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

VI. Gene Therapy

PH domain or its genetic sequences will also be useful in gene therapy (reviewed in Miller, Nature 357:455–460, (1992). Miller states that advances have resulted in practical approaches to human gene therapy that have demonstrated positive initial results. The basic science of gene therapy is described in Mulligan, Science 260:926–931, (1993).

In one preferred embodiment, an expression vector containing the PH domain coding sequence is inserted into cells, the cells are grown in vitro and then infused in large numbers into patients. In another preferred embodiment, a DNA segment containing a promoter of choice (for example a strong promoter) is transferred into cells containing an endogenous PH domain in such a manner that the promoter segment enhances expression of the endogenous PH domain gene (for example, the promoter segment is transferred to the cell such that it becomes directly linked to the endogenous PH domain gene).

The gene therapy may involve the use of an adenovirus containing PH domain cDNA targeted to a tumor, systemic PH domain increase by implantation of engineered cells, injection with PH domain virus, or injection of naked PH domain DNA into appropriate tissues.

Target cell populations may be modified by introducing altered forms of one or more components of the protein complexes in order to modulate the activity of such complexes. For example, by reducing or inhibiting a complex component activity within target cells, an abnormal signal transduction event(s) leading to a condition may be decreased, inhibited, or reversed. Deletion or missense mutants of a component, that retain the ability to interact with other components of the protein complexes but cannot function in signal transduction may be used to inhibit an abnormal, deleterious signal transduction event.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant PH domain protein into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, New York (1989), and in Ausubel et al., *Current Protocols in Molecular Biology*, Greene Publishing Associates and Wiley Interscience, New York (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi M R, Cell 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, Mol. Cell Biol. 7:2745–52 (1987)); electroporation, wherein cells are exposed to large voltage pulses to introduce holes into the membrane (Chu G. et al., Nucleic Acids Res., 15:1311–26 (1987)); lipofection/liposome fusion, wherein DNA is packaged into lipophilic vesicles which fuse with a target cell (Felgner P L., et al., Proc. Natl. Acad. Sci. U.S.A. 84:7413–7 (1987)); and particle bombardment using DNA bound to small projectiles (Yang N S. et al., Proc. Natl. Acad. Sci. 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T et al., Am. J. Respir. Cell. Mol. Biol., 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, antisense DNA or RNA, or enzymatically active RNA. Gene transfer can be performed in cultured cells or by direct administration into animals.

Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding PH domain is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

VII. Pharmaceutical Formulations and Modes of Administration

The particular compound, antibody, antisense or ribozyme molecule that affects the protein complexes and the disorder of interest can be administered to a patient either by themselves, or in pharmaceutical compositions where it is mixed with suitable carriers or excipient(s).

In treating a patient exhibiting an oncogenic disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, 1975, Ch. 1 p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The nucleic acid sequence encoding PH domain or binding partner can be administered prophylactically, or to patients having a disorder listed above, e.g., by exogenous delivery of the nucleic acid sequence encoding PH domain or binding partner as naked DNA, DNA associated with specific carriers, or in a nucleic acid expression vector to a desired tissue by means of an appropriate delivery vehicle, e.g., a liposome, by use of iontophoresis, electroporation and other pharmacologically approved methods of delivery. Routes of administration may include intramuscular, intravenous, aerosol, oral (tablet or pill form), topical, systemic, ocular, as a suppository, intraperitoneal and/or intrathecal.

Some methods of delivery that may be used include:

a. encapsulation in liposomes, b. transduction by retroviral vectors, c. localization to nuclear compartment utilizing nuclear targeting site found on most nuclear proteins, d. transfection of cells ex vivo with subsequent reimplantation or administration of the transfected cells, e. a DNA transporter system.

A PH domain or binding partner nucleic acid sequence may be administered utilizing an ex vivo approach whereby cells are removed from an animal, transduced with the PH domain or binding partner nucleic acid sequence and reimplanted into the animal. The liver can be accessed by an ex vivo approach by removing hepatocytes from an animal, transducing the hepatocytes in vitro with the PH domain or binding partner nucleic acid sequence and reimplanting them into the animal (e.g., as described for rabbits by Chowdhury et al, Science 254: 1802–1805, 1991, or in humans by Wilson, Hum. Gene Ther. 3: 179–222, 1992) incorporated herein by reference.

Many nonviral techniques for the delivery of a PH domain or binding partner nucleic acid sequence into a cell can be used, including direct naked DNA uptake (e.g., Wolff et al., Science 247: 1465–1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429–4432, 1987; Wu et al., J. Biol. Chem. 266: 14338–14342, 1991), and liposome-mediated delivery (e.g., Kaneda et al., Expt. Cell Res. 173: 56–69, 1987; Kaneda et al., Science 243: 375–378, 1989; Zhu et al., Science 261: 209–211, 1993). Many of these physical methods can be combined with one another and with viral techniques; enhancement of receptor-mediated DNA uptake can be effected, for example, by combining its use with adenovirus (Curiel et al., Proc. Natl. Acad. Sci. U.S.A. 88: 8850–8854, 1991; Cristiano et al., Proc. Natl. Acad. Sci. U.S.A. 90: 2122–2126, 1993).

The PH domain or binding partner or nucleic acid encoding such may also be administered via an implanted device that provides a support for growing cells. Thus, the cells may remain in the implanted device and still provide the useful and therapeutic agents of the present invention.

VIII. Identification of Agents

The complexes, components of such complexes, functional equivalents thereof, and/or cell lines that express such components and exhibit such protein complexes may be used to screen for additional compounds, antibodies, or other molecules capable of modulating the signal transduction event such complexes are involved in. Methods for purifying and/or producing such complexes, components of the complexes, functional equivalents thereof, and/or cell lines are described herein. The compounds, antibodies, or other molecules identified may, for example, act to disrupt the protein complexes of the invention (i.e., decrease or inhibit interactions between component members of the complexes, thereby causing physical separation of the components, and/or perturbing the activity of the complexes) or may lower the cellular level and/or decrease the activity of one or more of the components of such complexes.

Such compounds may include, but are not limited to, peptides made of D- and/or L-configuration amino acids (in, for example, the form of random peptide libraries; see Lam et al., Nature 354:82–84, 1991), phosphopeptides (in, for example, the form of random or partially degenerate, directed phosphopeptide libraries, see Songyang et al., Cell 767–778, 1993), antibodies, and small organic or inorganic molecules. Synthetic compounds, natural products, and other sources of potentially biologically active materials may be screened in a variety of ways, as described herein. The compounds, antibodies, or other molecules identified may be used as oncogenic disorder treatments, as described herein.

Compounds that bind to individual components, or functional portions of the individual components of the complexes (and may additionally be capable of disrupting complex formation) may be identified.

One such method included within the scope of the invention is a method for identifying an agent to be tested for an ability to modulate a signal transduction pathway disorder. The method involves exposing at least one agent to a protein comprising a functional portion of a member of the protein complex for a time sufficient to allow binding of the agent to the functional portion of the member; removing non-bound agents; and determining the presence of the compound bound to the functional portion of the member of the protein complex, thereby identifying an agent to be tested for an ability to modulate a disorder involving a polypeptide complex.

By "signal transduction disorder" is meant any disease or condition associated with an abnormality in a signal transduction pathway. The protein complex referred to below is a physical association of a PH domain and a PH domain binding partner. The level of interaction between the two components of the complex may be abnormal and thus cause the abnormality in the signal transduction pathway. Alternatively, the level of interaction between the complex components may be normal, but affecting that interaction may effectively treat a signal transduction pathway disorder.

The term "protein" refers to a compound formed of 5–50 or more amino acids joined together by peptide bonds. An "amino acid" is a subunit that is polymerized to form proteins and there are twenty amino acids that are universally found in proteins. The general formula for an amino acid is $H_2N$—CHR—COOH, in which the R group can be anything from a hydrogen atom (as in the amino acid glycine) to a complex ring (as in the amino acid tryptophan).

A functional portion of an individual component of the complexes may be defined here as a protein portion of an individual component of a complex still capable of forming a stable complex with another member of the complex under standard cellular and physiological conditions. For example, a functional portion of a component may include, but is not limited to, a protein portion of PH domain which is still capable of stably binding a PH domain ligand, and thus is still capable of forming a complex with that ligand. Further, in the case of the catalytic domains of the individual components of the invention, a functional portion of a catalytic domain may refer to a protein still capable of stably binding a substrate molecule under standard physiological conditions.

One method utilizing this approach that may be pursued in the isolation of such complex component-binding molecules would include the attachment of a component molecule, or a functional portion thereof, to a solid matrix, such as agarose or plastic beads, microtiter wells, petri dishes, or membranes composed of, for example, nylon or nitrocellulose, and the subsequent incubation of the attached component molecule in the presence of a potential component-binding compound or compounds. Attachment to said solid support may be direct or by means of a component specific antibody bound directly to the solid support. After incubation, unbound compounds are washed away, component-bound compounds are recovered. By utilizing this procedure, large numbers of types of molecules may be simultaneously screened for complex component-binding activity.

The complex components which may be utilized in the above screening method may include, but are not limited to, molecules or functional portions thereof, such as catalytic domains, phosphorylation domains, extra-cellular domains, or portions of extracellular domains, such as ligand-binding domains, and adaptor proteins, or functional portions thereof. The peptides used may be phosphorylated, e.g., may contain at least one phosphorylated amino acid residue, or may be unphosphorylated. A phosphorylation domain may be defined as a peptide region that is specifically phosphorylated at certain amino acid residues. A functional portion of such a phosphorylation domain may be defined as a peptide capable of being specifically phosphorylated at certain amino acids by a specific protein. Additionally, small molecule cellular metabolites, such as inositol phosphates, nucleotides, nucleosides, carbohydrates and lipids may be utilized in the screening method.

Molecules exhibiting binding activity may be further screened for an ability to disrupt protein complexes. Alternatively, molecules may be directly screened for an ability to promote the complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound. In addition, one could look for an increase in binding.

Additionally, complex formation in a whole cell may be assayed by utilizing co-immunoprecipitation techniques well known to those of skill in the art. Briefly, a cell line capable of forming a complex of interest may be exposed to a compound such as one identified as above, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

A preferred method for assessing modulation of complex formation within a cell utilizes a method similar to that described above. Briefly, a cell line capable of forming a complex of interest is exposed to a test compound. The cells are lysed and the lysate contacted with an antibody specific to one component of the complex, said antibody having been previously bound to a solid support. Unbound material is washed away, and the bound material is exposed to a second antibody, said second antibody binding specifically to a second component of the complex. The amount of second antibody bound is easily detected by techniques well known in the art. Cells exposed to an inhibitory test compound will have formed a lesser amount of complex compared to cells not exposed to the test compound, as measured by the amount of second antibody bound. Cells exposed to a test compound that promotes complex formation will have an increased amount of second antibody bound.

The effect of an agent on the differentiation capability of the complex of interest may be directly assayed. Such agents may, but are not required to, include those agents identified by utilizing the above screening technique. For example, an agent or agents may be administered to a cell such as a neuronal cell, capable of forming a complex, for example, which, in the absence of any agent, would not lead to the cell's differentiation. The differentiation state of the cell may then be measured either in vitro or in vivo. One method of measurement may involve observing the amount of neurile growth present.

Agents capable of disrupting complex formation and capable of reducing or inhibiting disorders, which involve the formation of such complexes, or which involve the lack of formation of such complexes, may be used in the treatment of patients exhibiting or at risk for such disorders. A sufficient amount of agent or agents such as those described above may be administered to a patient so that the symptoms of the disease or condition are reduced or eliminated.

IX. Purification and Production of Complexes

Described in this Section are methods for the synthesis or recombinant expression of components, or fragments thereof, of the protein complexes of the invention. Also described herein are methods by which cells exhibiting the protein complexes of the invention may be engineered.

The complexes of the invention may be substantially purified, i.e., may be purified away from at least 90% (on a weight basis), and from at least 99%, if desired, of other proteins, glycoproteins, and other macromolecules with which it is associated. Such purification can be achieved by utilizing a variety of procedures well known to those of skill in the art, such as subjecting cells, tissue or fluid containing the complex to a combination of standard methods, for example, ammonium sulfate precipitation, molecular sieve chromatography, and/or ion exchange chromatography.

Alternatively, or additionally, a complex may be purified by immunoaffinity chromatography using an immunoadsorbent column to which an antibody is immobilized which is capable of binding to one or more components of the complex. Such an antibody may be monoclonal or polyclonal in origin. Other useful types of affinity purification for the protein complex may utilize, for example, a solid-phase substrate which binds the catalytic kinase domain of a protein, or an immobilized binding site for noncatalytic domains of the components of the complex, which bind in such a manner as to not disrupt the complex. The complex of the present invention may be biochemically purified from a variety of cell or tissue sources.

X. Synthesis and Expression Methods

Methods for the synthesis of polypeptides or fragments thereof, which are capable of acting as components of the complexes of the present invention, are well-known to those of ordinary skill in the art. See, for example, Creighton, *Proteins: Structures and Molecular Principles*, W. H. Freeman and Co., New York (1983), which is incorporated herein, by reference, in its entirety.

Components of a complex which have been separately synthesized or recombinantly produced, may be reconstituted to form a complex by standard biochemical techniques well known to those skilled in the art. For example, samples containing the components of the complex may be combined in a solution buffered with greater than about 150 mM NaCl, at a physiological pH in the range of 7, at room temperature. For example, a buffer comprising 20 mM Tris-HCl, pH 7.4, 137 mM NaCl, 10% glycerol, 1% Triton X-100, 0.1% SDS, 0.5% deoxycholate and 2 mM EDTA could be used.

Methods for preparing the components of complexes of the invention by expressing nucleic acid encoding proteins are described herein. Methods which are well known to those skilled in the art can be used to construct expression vectors containing protein coding sequences and appropriate transcriptional and translational control signals. These methods include, for example, in vitro recombinant DNA techniques, synthetic techniques and in vivo recombination/genetic recombination. DNA and RNA synthesis may, additionally, be performed using an automated synthesizers. See, for example, the techniques described in Maniatis et al., *Molecular Cloning: A Laboratory Manual*, Cold Spring Harbor Laboratory, New York (1989), and in Ausubel et al., *Current Protocols in Molecular Biology*, Greene Publishing Associates and Wiley Interscience, New York (1989).

A variety of host-expression vector systems may be utilized to express the coding sequences of the components of the complexes of the invention. Such host-expression systems represent vehicles by which the coding sequences of interest may be produced, but also represent cells which may, when transformed or transfected with the appropriate nucleotide coding sequences, exhibit the protein complexes of the invention. These include but are not limited to microorganisms such as bacteria (e.g., *E. coli, B. subtilis*) transformed with recombinant bacteriophage DNA, plasmid DNA or cosmid DNA expression vectors containing protein coding sequences; yeast (e.g., Saccharomyces and Pichia) transformed with recombinant yeast expression vectors containing the protein coding sequences; insect cell systems infected with recombinant virus expression vectors (e.g., baculovirus) containing the protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the protein coding sequences coding sequence; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems a number of expression vectors may be advantageously selected depending upon the use intended for the complex being expressed. For example, when large quantities of complex proteins are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., *EMBO J.* 2:1791, 1983), in which the protein coding sequence may be ligated individually into the vector in frame with the lac Z coding region so that a fusion protein is produced; pIN vectors (Inouye and Inouye, *Nucleic acids Res.* 13:3101–3109, 1985; Van Heeke & Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned protein can be released from the GST moiety.

In an insect system, *Autographa californica* nuclear polyhedrosis virus (AcNPV) is used as a vector to express foreign genes. The virus grows in *Spodoptera frugiperda* cells. The complex coding sequence may be cloned individually into non-essential regions (for example the polyhedrin gene) of the virus and placed under control of an AcNPV promoter (for example the polyhedrin promoter). Successful insertion of the PH domain:binding partner complex coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., *J. Biol.* 46:584, 1983; Smith, U.S. Pat. No. 4,215,051).

In mammalian host cells, a number of viral based expression systems may be utilized. In cases where an adenovirus is used as an expression vector, the complex coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts. (E.g., See Logan & Shenk, *Proc. Natl. Acad. Sci. USA* 81:3655–3659, 1984) Specific initiation signals may also be required for efficient translation of inserted coding sequences. These signals include the ATG initiation codon and adjacent sequences.

In cases where an entire protein gene, including its own initiation codon and adjacent sequences, is inserted into the appropriate expression vector, no additional translational control signals may be needed. However, in cases where only a portion of the coding sequence is inserted, exogenous translational control signals, including the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987)

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably coexpress both the proteins may be engineered. Rather than using expression vectors which contain viral origins of replication, host cells can be transformed with the protein encoding DNA independently or coordinately controlled by appropriate expression control elements (e.g., promoter, enhancer, sequences, transcription terminators, polyadenylation sites, etc.), and a selectable marker.

Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which coexpress both the PH domain and binding partner. Such engineered cell lines are particularly useful in screening and evaluation of compounds that affect signals mediated by the complexes.

A number of selection systems may be used, including but not limited to the herpes simplex virus thymidine kinase (Wigler et al., *Cell* 11:223, 1977), hypoxanthine-guanine phosphoribosyltransferase (Szybalska & Szybalski, *Proc. Natl. Acad. Sci. USA* 48:2026, 1962), and adenine phosphoribosyltransferase (Lowy et al., *Cell* 22:817, 1980) genes can be employed in tk$^-$, hgprt$^-$ or aprt$^-$ cells, respectively. Also, antimetabolite resistance can be used as the basis of selection for dhfr, which confers resistance to methotrexate (Wigler et al., *Natl. Acad. Sci. USA* 77:3567, 1980; O'Hare et al., *Proc. Natl. Acad. Sci. USA* 78:1527, 1981); gpt, which confers resistance to mycophenolic acid (Mulligan & Berg, *Proc. Natl. Acad. Sci. USA* 78:2072, 1981); neo, which confers resistance to the aminoglycoside G-418 (Colberre-Garapin et al., *J. Mol. Biol.* 150:1, 1981); and hygro, which confers resistance to hygromycin (Santerre et al. *Gene* 30:147, 1984) genes.

New members of the protein families capable of forming the complexes of the invention may be identified and isolated by molecular biological techniques well known in the art. For example, a previously unknown protein encoding gene may be isolated by performing a polymerase chain reaction (PCR) using two degenerate oligonucleotide primer pools designed on the basis of highly conserved sequences within domains common to members of the protein family.

The template for the reaction may be cDNA obtained by reverse transcription of mRNA prepared from cell lines or tissue known to express complexes. The PCR product may be subcloned and sequenced to insure that the amplified sequences represent the sequences of a member of the PTK or adaptor subfamily. The PCR fragment may then be used to isolate a full length protein cDNA clone by radioactively labeling the amplified fragment and screening a bacteriophage cDNA library. Alternatively, the labeled fragment may be used to screen a genomic library. For a review of cloning strategies which may be used. See e.g., Maniatis, *Molecular Cloning: A Laboratory Manual*, Cold Springs Harbor Press, New York (1989); and Ausubel et al., *Current Protocols in Molecular Biology*, Green Publishing Associates and Wiley Interscience, New York (1989). A general method for cloning previously unknown proteins has been described by Skolnik (Skolnik, E. Y., *Cell* 65:75, 1991) and Skolnik et al., (U.S. patent application Ser. No. 07/643,237) which are incorporated herein by reference, in their entirety, including drawings.

XI. Derivatives of Complexes

Also provided herein are functional derivatives of a complex. By "functional derivative" is meant a "chemical derivative," "fragment," "variant," "chimera," or "hybrid" of the complex, which terms are defined below. A functional derivative retains at least a portion of the function of the protein, for example reactivity with an antibody specific for the complex, enzymatic activity or binding activity mediated through noncatalytic domains, which permits its utility in accordance with the present invention.

A "chemical derivative" of the complex contains additional chemical moieties not normally a part of the protein. Covalent modifications of the protein complex or peptides are included within the scope of this invention. Such modifications may be introduced into the molecule by reacting targeted amino acid residues of the peptide with an organic derivatizing agent that is capable of reacting with selected side chains or terminal residues, as described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect or reversing the charge of the lysinyl residues. Other suitable reagents for derivatizing primary amine containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $\phi K_\alpha$ of the guanidine functional group. Furthermore, these reagents may react with the groups of lysine as well as the arginine alpha-amino group.

Tyrosyl residues are well-known targets of modification for introduction of spectral labels by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction carbodiimide (R'—N—C—N—R') such as 1-cyclohexyl-3-(2-morpholinyl(4-ethyl) carbodiimide or 1-ethyl-3-(4-azonia-4,4-dimethylpentyl) carbodiimide. Furthermore, aspartyl and glutamyl residue are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful, for example, for cross-linking the component peptides of the complexes to each other or the complex to a water-insoluble support matrix or to other macromolecular carriers. Commonly used cross-linking agents include, for example, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[p-azidophenyl)dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (Creighton, T. E., Proteins: Structure and Molecular Properties, W. H. Freeman & Co., San Francisco, pp. 79–86 (1983)), acetylation of the N-terminal amine, and, in some instances, amidation of the C-terminal carboxyl groups.

Such derivatized moieties may improve the stability, solubility, absorption, biological half life, and the like. The moieties may alternatively eliminate or attenuate any undesirable side effect of the protein complex and the like. Moieties capable of mediating such effects are disclosed, for example, in *Remington's Pharmaceutical Sciences,* 18th ed., Mack Publishing Co., Easton, Pa. (1990).

The term "fragment" is used to indicate a polypeptide derived from the amino acid sequence of the proteins, of the complexes having a length less than the full-length polypeptide from which it has been derived. Such a fragment may, for example, be produced by proteolytic cleavage of the full-length protein. Preferably, the fragment is obtained recombinantly by appropriately modifying the DNA sequence encoding the proteins to delete one or more amino acids at one or more sites of the C-terminus, N-terminus, and/or within the native sequence. Fragments of a protein, when present in a complex resembling the naturally occurring complex, are useful for screening for compounds that act to modulate signal transduction, as described below. It is understood that such fragments, when present in a complex may retain one or more characterizing portions of the native complex. Examples of such retained characteristics include: catalytic activity; substrate specificity; interaction with other molecules in the intact cell;

regulatory functions; or binding with an antibody specific for the native complex, or an epitope thereof.

Another functional derivative intended to be within the scope of the present invention is a complex comprising at least one "variant" polypeptide which either lack one or more amino acids or contain additional or substituted amino acids relative to the native polypeptide. The variant may be derived from a naturally occurring complex component by appropriately modifying the protein DNA coding sequence to add, remove, and/or to modify codons for one or more amino acids at one or more sites of the C-terminus, N-terminus, and/or within the native sequence. It is understood that such variants having added, substituted and/or additional amino acids retain one or more characterizing portions of the native complex, as described above.

A functional derivative of complexes comprising proteins with deleted, inserted and/or substituted amino acid residues may be prepared using standard techniques well-known to those of ordinary skill in the art. For example, the modified components of the functional derivatives may be produced using site-directed mutagenesis techniques (as exemplified by Adelman et al., 1983, DNA 2:183) wherein nucleotides in the DNA coding the sequence are modified such that a modified coding sequence is modified, and thereafter expressing this recombinant DNA in a prokaryotic or eukaryotic host cell, using techniques such as those described above. Alternatively, components of functional derivatives of complexes with amino acid deletions, insertions and/or substitutions may be conveniently prepared by direct chemical synthesis, using methods well-known in the art. The functional derivatives of the complexes typically exhibit the same qualitative biological activity as the native complexes.

XII. Evaluation of Disorders

The protein complexes of the invention involved in disorders may be utilized in developing a prognostic evaluation of the condition of a patient suspected of exhibiting such a disorder. For example, biological samples obtained from patients suspected of exhibiting a disorder involving a protein complex may be assayed for the presence of such complexes. If such a protein complex is normally present, and the development of the disorder is caused by an abnormal quantity of the complex, the assay should compare complex levels in the biological sample to the range expected in normal tissue of the same cell type.

Among the assays which may be undertaken may include, but are not limited to isolation of the protein complex of interest from the biological sample, or assaying for the presence of the complex by exposing the sample to an antibody specific for the complex, but non-reactive to any single, non-complexed component, and detecting whether antibody has specifically bound.

Alternatively, one or more of the components of the protein complex may be present in an abnormal level or in a modified form, relative to the level or form expected is normal, nononcogenic tissue of the same cell type. It is possible that overexpression of both components may indicate a particularly aggressive disorder. Thus, an assessment of the individual and levels of mRNA and protein in diseased tissue cells may provide valuable clues as to the course of action to be undertaken in treatment of such a disorder. Assays of this type are well known to those of skill in the art, and may include, but are not limited to, Northern blot analysis, RNAse protection assays, and PCR for determining mRNA levels. Assays determining protein levels are also well known to those of skill in the art, and may include, but are not limited to, Western blot analysis, immunoprecipitation, and ELISA analysis. Each of these techniques may also reveal potential differences in the form (e.g., the primary, secondary, or tertiary amino acid sequence, and/or post-translational modifications of the sequence) of the component(s).

EXAMPLES

The examples below are non-limiting and are merely representative of various aspects and features of the present invention. The examples below demonstrate the specific high affinity interaction of PH domains with binding partners.

The PH domains from PLC-$\delta_1$, and dynamin, as well as the N-terminal PH domain of pleckstrin (PLC$\delta$-PH, Dyn-PH and PlecN-PH respectively) were expressed in *Escherichia* coli, using the T7 expression system (Studier et al., 1990), and purified as described herein. Determination of the structure of PlecN-PH by NMR (Yoon H. S. et al., Nature 369, 672–675, 1994) and of Dyn-PH by NMR and X-ray crystallography. Downing, A. K. et al., Curr. Biol. 4, 884–891, 1994; Fushman, D. et al., *Proc. Natl. Acad. Sci. USA* 92, 816–820, 1995; Timm, D. et al., *Nature Struct. Biol.* 1, 782–788, 1994; Ferguson, K. M. et al., *Cell*, 79, 199–209, 1994) has shown that both have very similar structures. Circular dichroism (CD) analysis of PLC-PH, Dyn-PH and PlecN-PH shows that the secondary-APH, Dyn-PH and PlecN-PH shows that the secondary+δ-1 structure content of each PH domain is very similar. APH, Dyn-PH and PlecN-PH shows that the secondary+δ-1+1 An alignment of PLCδ-PH with the PH domains of known structure is presented in FIG. 1.

Example 1
Generation of Recombinant PH Domains

Dynamin PH and the Lck SH2 domain were produced exactly as described (Ferguson, K. M. et al., *Cell*, 79, 199–209, 1994; Lemmon, M. A. and Ladbury, J. E., *Biochemistry* 33, 5070–5076, 1994. For rat PLC-$\delta_1$ and human pleckstrin, the polymerase chain reaction was utilized to amplify from the respective cDNA a fragment corresponding to the PH domain desired (residues 20–136 of PLC-$\delta_1$ (PLC-δPH), and residues 1–110 of pleckstrin (PlecN-PH). An Nδε I site was incorporated at the 5' end of the coding sequence, adding an initiator methionine to the native coding sequence, and a Bam HI site at the 3' end. The resulting fragment was digested with NδεI and BaμHI, and was ligated into appropriately digested pET11α (Studier et al., 1990), for expression directed by the phage T7 promoter.

Each PH domain was expressed from such a construct and purified as described (Lemmon, M. A. and Ladbury, J. E., *Biochemistry* 33, 5070–5076, 1994; Ferguson, K. M. et al., *Cell*, 79, 199–209, 1994). The only difference was that different gradients of NaCl were required for elution of the different PH domain from the cation exchange column. PLCδ-PH eluted at approximately 200 mM NaCl, and PlecN-PH at approximately 600 mM NaCl. After a final gel-filtration step, each PH domain was at least 99% pure, as assessed on overloaded Coomassie-stained SDS-gels. Concentrations of PH domains were determined by measuring absorbance at 278 nm, and using the extinction coefficient calculated from the tryptophan and tyrosine content of each domain.

Example 2
Inositol Phosphate and Vesicle Preparations

D-I(145)$P_3$, 1-(a-glycerophosphoryl)-D-inositol-4,5-bisphosphate (GPIP$_2$), D-I(134)$P_3$, D-I(245)$P_3$, D-I(156)$P_3$, D-I(1346)$P_4$, D-I(3456)$P_4$, and D-I(13456)$P_5$ and 1-(a-glycerophosphoryl)-inositol (GPI) were purchased from Calbiochem. L-I(145)$P_3$, D-I(123456)$P_6$, D-I(1256)$P_4$, D-I(24)$P_2$, D-I(14)$P_2$, D-I(45)$P_2$, D-I(1345)$P_4$, inositol-2-phosphate and inositol hexasulfate were from Sigma. Inositol polyphosphates were used without further purification. All inositol polyphosphates are named as their D-isomer unless stated otherwise. Concentrations of inositol phosphates used were based upon the mass and composition stated by the supplier.

Phosphatidylinositol-(4,5)-bisphosphate (PIP$_2$) was purchased from Calbiochem, and phosphatidylinositol-4-phosphate (PIP) was purchased from Sigma. All other lipids were from Avanti Polar Lipids (Birmingham, Ala.). To generate vesicle suspensions, lipids were dissolved at 5 mg/ml in 50:50 v/v chloroform:methanol, and mixed to generate solutions that were 95% synthetic DMPC, 5% PS, PI, PIP, or PIP$_2$. 0.25% HCl was added to the solutions containing PIP and PIP$_2$ to protonate the phosphate groups and render them soluble. The mixtures (plus 100% DMPC) were dried overnight in glass tubes in a SpeedVac, and rehydrated with 50 mM MOPS, 100 mM NaCl, pH 6.8, to a final lipid concentration of 20 mg/ml. The pH of each suspension was checked, and corrected if necessary. Microprobe- as well as bath-sonication, together with several rounds of freezing and thawing was then used to generate a homogeneous, transparent suspension of vesicles.

Example 3
Gel Filtration and Spin-Column Competition Experiments

1-$^3$H-labeled I(145)$P_3$ and I(134)$P_3$ were purchased from NEN (21 Ci/mmol, 0.48 μM). For gel-filtration studies, PH domain at 10 μM was mixed with 20 μM IP$_3$, containing 100 nCi of the appropriate $^3$H-labeled isomer. A 200 μl sample was applied to a BioRad BiogelP6 desalting column, and 40 fractions of 300 μl were collected. A Bio-Rad protein assay was performed on 50 ml of each fraction to determine the elution position of the protein, and scintillation counting of the remainder was used to detect the elution positions of IP$_3$. Experiments were performed in either 50 mM MOPS, 100 mM NaCl, pH 6.8, or 100 mM NH$_4$OAc, pH 6.8. The results were identical in each case.

For the competition assay, a 40 μM solution of PLCδ-PH, also containing 40 μM I(145)$P_3$ was prepared in 50 mM MOPS. 100 mM NaCl, pH 6.8, and 1-$^3$H-I(145)P3 was added (40 nCi, 48 nM). This was then diluted to 10 μM PLCδ-PH in 30 μl samples containing competitor such that in the final 40 μl sample, the molar excess of competitor over I(145)$P_3$ (present at 10 μM) was that plotted in FIG. 3. The sample was then applied to a pre-spun 1 ml spin-column containing Biogel P6 desalting medium. The spin-column was then centrifuged for 4 minutes at 900 g. Essentially all of the protein was determined to pass through the column under these conditions, and no significant counts were seen to pass through the column in the absence of protein. After spinning, all of the material that passed through the column was added to scintillation fluid for counting. Counts were normalized to those obtained in the absence of competitor, and plotted as fraction of maximal binding.

Example 4
Isothermal Titration Calorimetry

All experiments utilized the OMEGA instrument from MicroCal (Wiseman, T. et al., *Anal. Biochem.* 179, 131–137, 1989), in the laboratory of Prof. Julian Sturtevant at Yale. Titrations were performed at 25° C. in 50 mM MOPS, 100 mM NaCl, pH 6.8 or 100 mM NH$_4$OAc at pH 6.8. There was no significant difference between the two conditions for any titration. For each titration, PH domain solution was dialyzed exhaustively against the buffer used for dilution of highly concentrated stocks of ligand. Heats for dilution of the ligand solutions were determined in separate titrations of ligand into buffer solution present in the cell. For all titrations reported, the heats per injection remained constant throughout such a dilution experiment, and a mean value for this heat was subtracted from those measured in the binding titration.

Figure 2A:
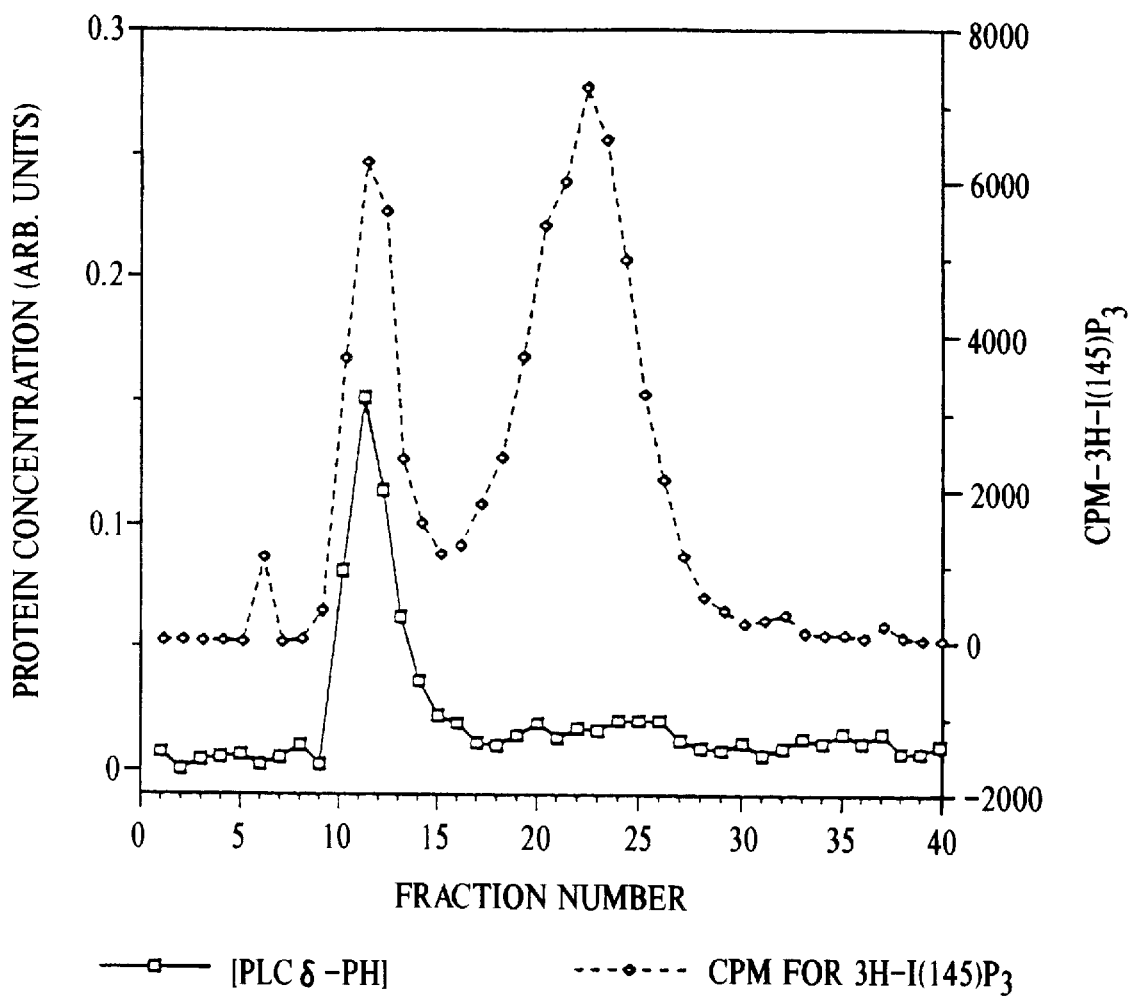
FIG. 2A was obtained after $^3H-I(145)P_3$ (20 μM) was mixed with PLCδ-PH (10 μM), and applied to a gel-filtration column. Fractions were assayed for protein content (solid line) and for $^3H-I(145)P_3$ content by scintillation counting (broken line). Approximately 40% of the $I(145)P_3$ added was seen to coelute with PLCδ-PH.
Figure 2B:
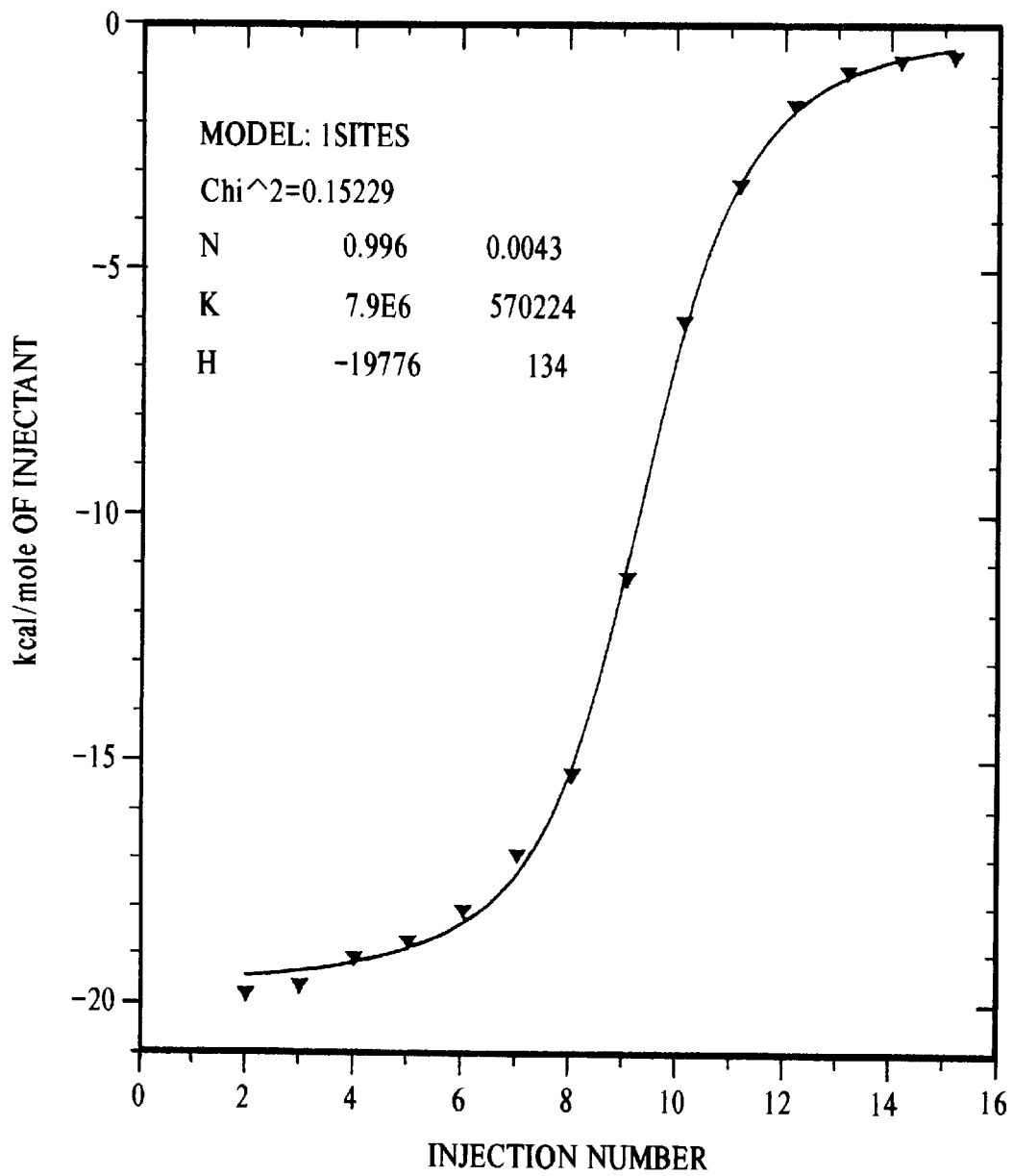
FIG. 2B shows a typical binding isotherm obtained using ITC for $I(145)P_3$ binding to PLCδ-PH. 15×16 ml injections of $I(145)P_3$ (100 μM) were made into a solution of PLCδ-PH (11 μM) in the calorimeter cell (1.39 μl). The resulting titration curve was fit using Omega software (Wiseman, T. et al., *Anal. Biochem.* 179, 131–137, 1989), giving values for stoichiometry, binding constant and ΔH (see Table 1).

A typical titration, as presented in FIG. 2B, employed 10 μM PLCδ-PH in the calorimeter cell, and 100 μM I(145)P3 in the calorimeter syringe. Higher concentrations were employed for weaker binding events. In all cases, the value for [sites]/$K_D$ (c-value) was between 10 and 60. Titration curves were fit using ORIGIN software (MicroCal), using a nonlinear least squares algorithm based on a model for a single class of binding site, as indicated by the shape of the titrations (Wiseman, T. et al., *Anal. Biochem.* 179, 131–137, 1989). Stoichiometry, binding constant ($K_B$) and $\Delta H$ were all allowed to float in the fitting procedure.

Example 6
Gel Filtration and Centrifugation Studies of PH Domain Binding to Vesicles Attempts to detect PH domain association with lipid vesicles were performed exactly as described by Harlan, J. E. et al., *Nature* 371, 168–170, 1994. In addition to using the BCA protein assay reagent, for which lipid blanks were rather high compared with the values expected for the protein concentrations employed, we also measured $OD_{278}$ of the supernatants after addition of SDS in order to detect removal of protein upon pelleting vesicles.

For gel filtration studies, a 150×8 mm UltroGel AcA 44 (Spectrum) was employed for low pressure studies. In addition, a 150×7.5 mm Superdex 75 (Pharmacia) column was packed for HPLC analysis. PH domains at 20 $\mu$M and higher were mixed with an approximate 20-fold molar excess of the tested phospholipid (at 5% in DMPC vesicles) in a total volume of 100 $\mu$l, and applied to the column. The size of the protein peak with and without lipid added in the column load was compared as a monitor of binding. In addition, fractions containing lipid were collected, dissolved in 2% SDS, and analyzed for the presence of a protein absorption spectrum. Since no lipid binding could be detected under these conditions, we further employed the equilibrium gel filtration method of Hummel, J. P., and Dreyer, W. J., Biochim. Biophys. Acta. 63, 530–532, 1962, incorporated herein by reference in its entirety, including any drawings.

A 150×7.5 mm Superdex 75 column, attached to a Dionex HPLC system, was equilibrated with buffer containing PH domain at around 5 $\mu$M (depending upon the experiment). A suspension of vesicles that also contained 5 $\mu$M PH domain was then injected. In the absence of interaction between the PH domain and the vesicles, the resulting column profile (detected by absorbance at 280 nm) reflects only the lipid peak. However, if there is significant interaction, a trough is observed at a position corresponding to the elution position of the free PH domain, since the lipids have removed free PH domain from the column buffer. When such a trough was observed, in order to determine a $K_D$ for the interaction, a series of higher concentrations of PH domain were injected, all with constant lipid concentration. A plot of trough area against [PH] in the injected sample was linear, becoming positive when excess free protein was present in the injected sample (see FIG. 5B). This line was used to determine the point at which no trough was observed. At this point, $[PH]_{free}$ in the injected sample is equal to [PH] in the column buffer. Since $[PH]_{total}$ as well as $[lipid]_{total}$ in the injected sample are known, $K_D$ can be determined, as $K_D=([PH]_{free} \times [lipid]_{free})/[complex]$, $[complex]=[PH]_{total}-[PH]_{free}$, and $[lipid]_{free}=[lipid]_{total}-[complex]$.

Example 7
I(145)P$_3$ Binds with High Affinity to PLC$\delta$-PH, but not to the PH Domains of Dynamin or Pleckstrin I(145)P$_3$ is known to bind to a region in the amino-terminus of PLC-d$_1$ that includes the PH domain, and this binding results in inhibition of the enzyme. We determined the isolated PH domain itself could bind to I(145)P$_3$. PLC$\delta$-PH at 10 $\mu$M was mixed with a two-fold excess of I(145)P$_3$, containing $^3$H-labeled I(145)P$_3$, and the mixture was run on a Biogel-P6 desalting column, as shown in FIG. 2A. Approximately 40% of the applied counts were seen to co-elute with PLC$\delta$-PH, demonstrating that there is significant binding at the concentration used for this assay. Using the same approach, no binding of I(134)P$_3$ to PLC$\delta$-PH could be detected. Furthermore, neither Dyn-PH nor PlecN-PH was seen to bind to I(145)P$_3$ or I(134)P3. These observations thus show that IP$_3$ binding to the PLC$\delta_1$ PH domain is specific with respect to both the PH domain and the IP$_3$ isomer.

To determine the affinity of I(145)P$_3$ binding to PLC$\delta$-PH, we employed the technique of isothermal titration calorimetry (ITC), in which the heat liberated (or absorbed) upon binding is measured as small aliquots of ligand (I(145)P$_3$) are added to a solution of the macromolecule (PLC$\delta$-PH) at known concentration and at constant temperature. A titration curve is generated such as that to an equation describing a simple binding reaction (Wiseman, T. et al., *Anal. Biochem.* 179, 131–137, 1989). From this fit, values for the binding constant, stoichiometry and $\Delta H$ for the binding reaction are ascertained. From several titrations, including that presented in FIG. 2B, we find that PLC$\delta$-PH binds to I(145)P$_3$ with a stoichiometry of 1:1, dissociation constant ($K_D$) of 200 nM, and $\Delta H$ of −19 kcal/mol (Table 1). Binding is therefore entirely enthalpy-driven, and the affinity of I(145)P$_3$ for PLC$\delta$-PH is only about five-fold weaker than the value of ≈40 nM reported for its binding to the purified I(145)P$_3$-receptor. Ferris, C. D. et al, *Nature*, 342, 87–89, 1989.

Example 8
Specificity of Inositol Polyphosphate Binding to PLC$\delta$-PH

Figure 3:
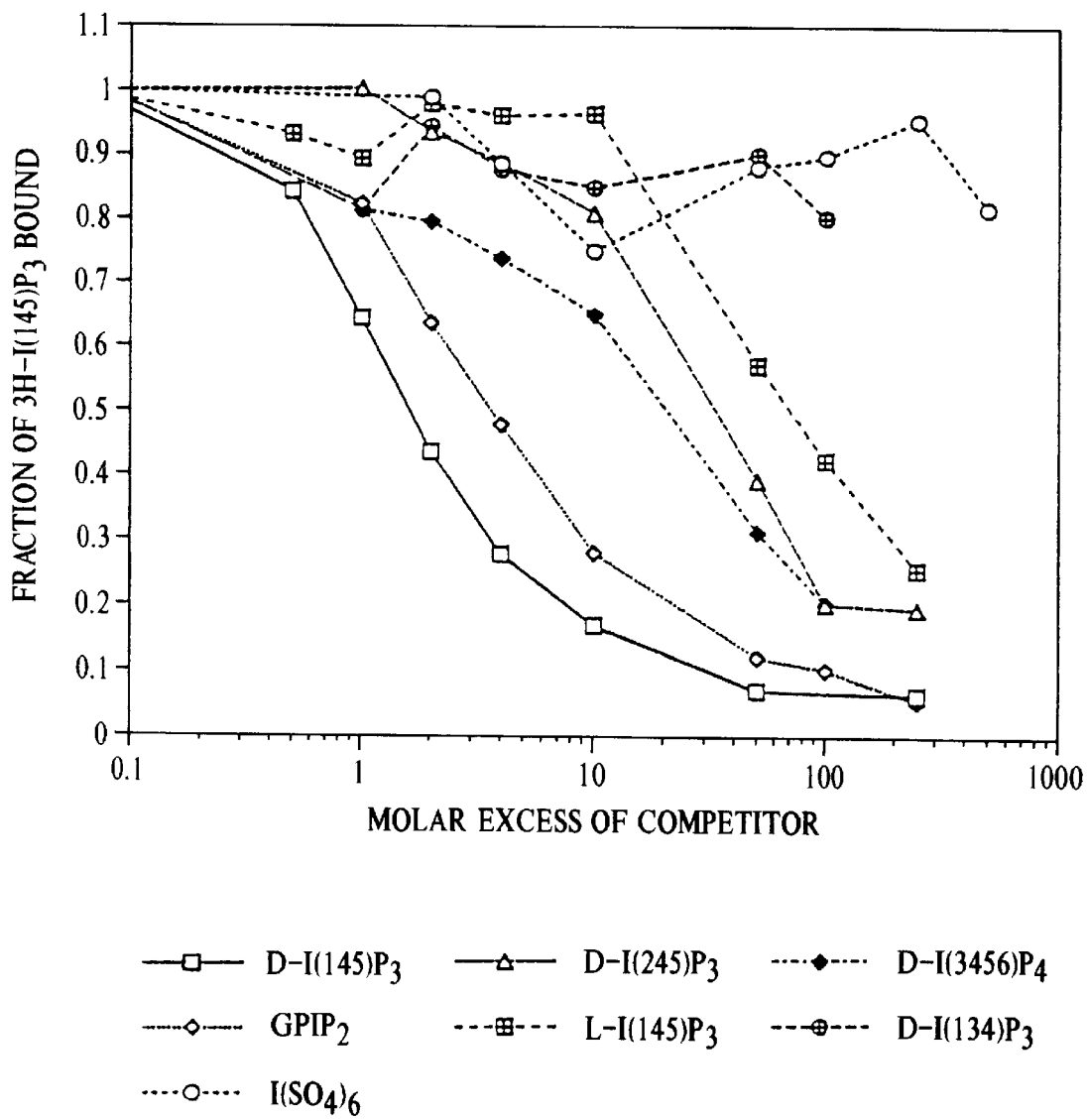
FIG. 3 shows an analysis of the specificity for $I(145)P_3$ binding using a competition assay. A spin-column based competition assay was employed to determine relative affinities of other inositol polyphosphates for PLCδ-PH. PLCδ-PH (10 μM) was incubated with $I(145)P_3$ (10 μM), containing $^3H-I(145)P_3$ and the indicated molar excess of competitor (cold $I(145)P_3$ for the $I(145)P_3$ curve). The sample (40 μl) was then applied to a Biogel P6 gel filtration spin-column. After centrifugation all protein is recovered, while unbound $I(145)P_3$ remains in the column. For each reaction, the total number of $^3H-I(145)P_3$-derived counts passing through the column was determined by scintillation counting. This number was divided by the number of counts eluting with protein in the absence of added competitor to give the fraction of $^3H-I(145)P_3$ bound. Data are presented for all of the inositol trisphosphates studied, together with data for competition by $I(3456)P_4$ and inositol hexasulfate. Each curve represents the mean of two or more experiments. $K_D$ values estimated using this approach for other inositol polyphosphates are presented in Table 2.

To establish the degree of specificity of I(145)P$_3$ binding to PLC$\delta$-PH, we used a spin-column based competition-assay, as described herein, to determine the relative dissociation constants of a number of different inositol polyphosphates. This analysis clearly demonstrated that PLC$\delta$-PH is specific for I(145)P$_3$ (FIG. 3 and Table 2). Compounds with fewer than three phosphate groups, including I(4,5)P$_2$ and I(1,4)P$_2$, showed no detectable binding, giving them a $K_D$ weaker than 50 $\mu$M. I(134)P$_3$ showed similarly weak competition, whereas I(245)P$_3$ and L-myo-I(145)P$_3$ were able to compete more effectively for D-myo I(145)P$_3$ binding.

The concentrations required to reduce $^3$H-I(145)P$_3$ binding by 50% suggest $K_D$ values for I(245)P$_3$ and L-myo-I(145)P$_3$ of 7.5 $\mu$M and 13 $\mu$M respectively. Indeed, for those inositol phosphates that were capable of competing for I(145)P$_3$ binding to PLC$\delta$-PH to an extent detectable in our assay, all bound with apparent $K_D$ values between 4 $\mu$M and 13 $\mu$M—a full 20–60 fold weaker than I(145)P$_3$, clearly indicating specific binding. The nature and degree of specificity seen for inositol phosphate binding by PLC$\delta$-PH is very similar to that reported for whole PLC$\delta_1$. Cifuentes, M. E. et al., *J. Biol. Chem.* 269, 1945–1948, 1994; Yagisawa, H. et al., *J. Biol. Chem.* 269, 20179–20188, 1994) as well as for the I(145)P$_3$-receptor (Lu et al., 1994).

The presence of phosphate groups at both the 4- and 5-positions appears to be necessary, but not sufficient, for significant binding. Since I(45)P$_2$ does not bind detectably, additional phosphates are clearly required. Addition of a phosphate group at the 1-position gives high-affinity binding, whereas a third phosphate elsewhere, or addition of further phosphate groups to I(145)P$_3$, leads to micromolar-range affinities. The fact that inositol hexasulfate, even at a 500-fold molar excess over I(145)P$_3$, did not detectably reduce I(145)P$_3$ binding suggests that the competition observed here is not simply a result of increased ionic strength. Indeed, I(145)P$_3$ binding was only reduced by approximately 40% in the presence of 1M NaCl.

The only soluble inositol phosphate tested with a $K_D$ less than ten-fold weaker than that for I(145)P$_3$ binding was 1-(α-glycerophosphoryl)-inositol (4,5)$P_2$ (GPI$P_2$), which binds to PLCδ-PH with a $K_D$ of 400 nM, as assessed by the spin-column competition assay (Table 2) and ITC (Table 1). GPI$P_2$ is the product of PI$P_2$ hydrolysis by phospholipase D, and represents I(145)$P_3$ with a glycerol moiety esterified to the 1-phosphate. Since this alteration weakens its binding to PLCδ-PH by just two-fold, it is reasonable to expect that PLCδ-PH should bind also to PI$P_2$ itself.

Example 9
PH Domain Binding to Inositol Phospholipids

Since PLCδ-PH binds to GPI$P_2$, we also analyzed its binding to lipid vesicles that contain inositol phospholipids. Initially, we performed a centrifugation-based assay, using the conditions described by Harlan, J. E. et al., Nature 371, 168–170, 1994. We could detect no binding in this assay of any PH domain to PI$P_2$, phosphatidyinositol-4-phosphate (PIP), phosphatidylinositol (PI) or phosphatidylserine (PS), each at 5% in vesicles of dimyristoylphosphatidylcholine (DMPC). Similarly, we were unable to detect association of any of the PH domains with the same vesicles by using size-exclusion chromatography to separate protein and lipid. Any complexes between the PH domains and these vesicles therefore form with low affinity and/or have fast dissociation kinetics, such that they dissociate in the separation methods employed.

These negative results are at odds with the report of Harlan, J. E. et al., Nature 371, 168–170, 1994 for PlecN-PH, and we have no explanation for the discrepancy. Our inability to detect binding of PLCδ-PH was also unexpected, since whole PLC-$\delta_1$ has been found to sediment with sucrose-loaded PI$P_2$-containing vesicles with an apparent $K_D$ of approximately 2.5 μM (Rebecchi, M. et al., Biochemistry 31, 12742–12747, 1992). This difference would be explained if regions of PLC-$\delta_1$ other than the PH domain also have affinity for PI$P_2$. Such additional low-affinity PI$P_2$ binding contributed by the remainder of the protein (such as the catalytic binding site) would reduce the dissociation rate (and increase affinity), such that the complex between whole PLC-$\delta_1$ and PIP2-containing vesicles can be separated from free PLC-$\delta_1$ by centrifugation. Indeed, proteolytic removal of the amino-terminal portion of PLC-$\delta_1$ does not completely obliterate PIP2 binding of the enzyme. Cifuentes, M. E. et al., J. Biol. Chem. 268, 11586–11593, 1993.

Figure 4A:
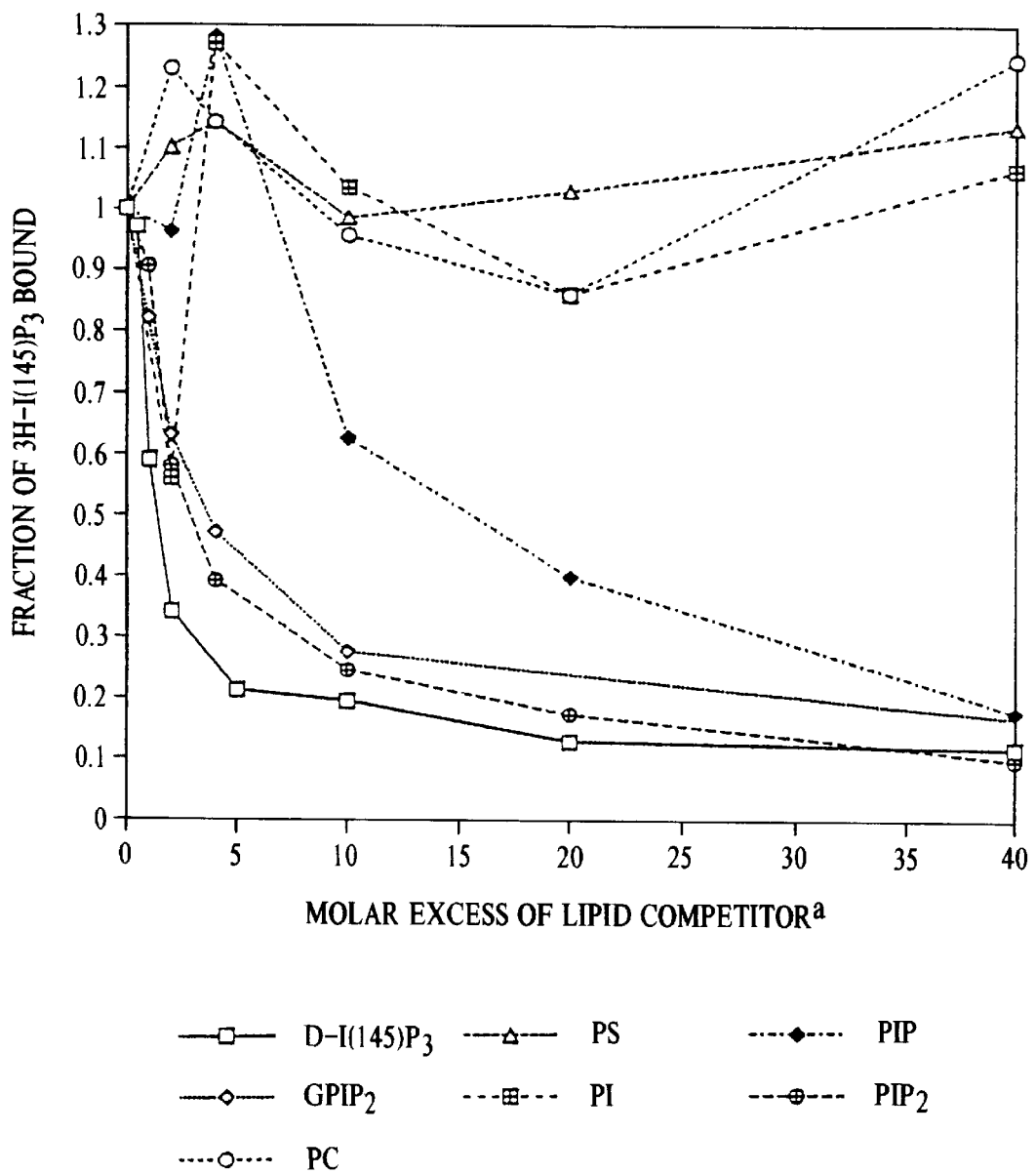
FIG. 4A shows competition experiments showing that $PIP_2$-containing vesicles can compete for $I(145)P_3$ binding to PLCδ-PH as effectively as can $GPIP_2$. PIP-containing vesicles can also compete, although about 15-fold less effectively. By contrast, vesicles containing 5% PS or 5% PI, as well as pure DMPC vesicles did not compete for $I(145)P_3$ binding at up to 40-fold molar excesses (assuming 50% of lipid is on the surface of the vesicle). Molar excess is plotted on a linear scale, by contrast with FIG. 3, since the maximum molar excess used was smaller.

Cifuentes, M. E. et al., J. Biol. Chem. 269, 1945–1948, 1994 showed that I(145)$P_3$ inhibits binding of whole PLC-$\delta_1$ to PI$P_2$-containing vesicles. Furthermore, Yagisawa, H. et al., J. Biol. Chem. 269, 20179–20188, 1994) showed that PI$P_2$-containing vesicles could inhibit the binding of whole PLC-$\delta_1$ to I(145)$P_3$. Amino-terminal deletion abolishes this behavior. We used the spin-column competition assay described above, to determine whether PI$P_2$ and several other phospholipids could compete for the binding of I(145) $P_3$ to isolated PLCδ-PH. As shown in FIG. 4A, vesicles containing PC alone, PI at 5% or PS at 5% showed no detectable competition at up to 2-fold molar excesses over I(145)$P_3$. 5% PIP-containing vesicles competed weakly, suggesting that they have are capable of low-affinity interaction with PLCδ-PH. By contrast, DMPC vesicles containing 5% PI$P_2$ showed competition that was almost as effective as that seen with unlabelled I(145)$P_3$. Assuming that 50% of the PI$P_2$ in the vesicles is available for PLCδ-PH binding (i.e. on the outside of the vesicles), the apparent $K_D$ for PI$P_2$ binding to PLCδ-PH is approximately equal to that measured for GPI$P_2$ (400 nM), or just two-fold weaker than that for I(145)$P_3$. Thus PI$P_2$ in lipid vesicles binds to PLCδ-PH in a specific manner that is mutually exclusive with I(145)$P_3$ binding, as shown for whole PLC-$\delta_1$. Cifuentes, M. E. et al., J. Biol. Chem. 269, 1945–1948, 1994; Yagisawa, H. et al., J. Biol. Chem. 269, 20179–20188, 1994).

Figure 4B:
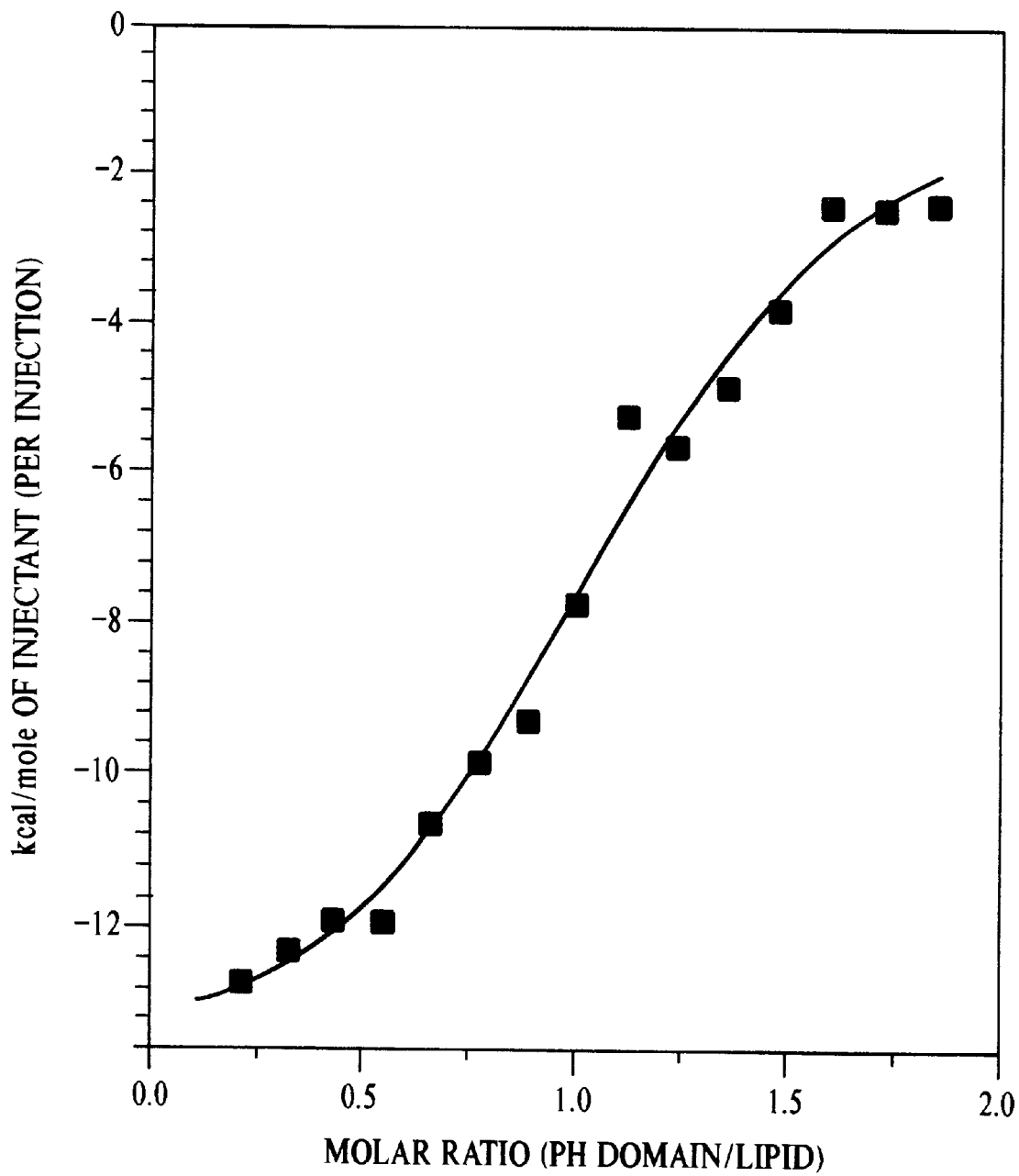
FIG. 4B shows ITC of PLCδ-PH binding to $PIP_2$-containing vesicles. A typical binding isotherm obtained using ITC for PLCδ-PH binding to $PIP_2$-containing vesicles. 15×16 μl aliquots of PLCδ-PH (120 μM) were injected into a bath-sonicated suspension of DPMC vesicles containing 5% $PIP_2$ at 25° C. Assuming that 50% of the $PIP_2$ is available for PLCδ-PH binding, $[PIP_2]$ was 12 μM. The resulting titration curve was fit using Omega software (Wiseman et al., 1989). $K_D$ for this titration was 0.95 μM, stoichiometry 0.88:1, and delta H −13.6 kcal/mol (see Table 1).

In order to determine directly the binding constant and thermodynamic parameters for PI$P_2$ binding to PLCδ-PH we used ITC. As shown in FIG. 4B, ITC confirmed that PLCδ-PH binds to PI$P_2$ at 5% in DMPC vesicles with a $K_D$ of 1 μM. The apparent stoichiometry indicated that 57% of PI$P_2$ in the vesicle preparation was available for PLCδ-PH binding. As for I(145)$P_3$ and GPI$P_2$ binding, the reaction was entirely enthalpy driven ($\Delta H = -10$ kcal/mol), consistent with their modes of interaction being identical.

We also utilized the equilibrium gel-filtration approach described by Hummel, J. P., and Dreyer, W. J., Biochim. Biophys. Acta. 63, 530–532, 1962. In this approach, a size exclusion column is equilibrated with a solution of the ligand (5 μM PH domain in this case), and a solution of macromolecule (a vesicle suspension in this case) that also contains 5 μM ligand is then injected. In the absence of interaction between the ligand and macromolecule, a single peak, corresponding to the macromolecule, is observed. However, if there is significant interaction, a trough is observed at a position corresponding to the elution position of the free ligand, since the macromolecule has removed ligand from the column buffer. If an interaction is observed, its $K_D$ can be determined as described in Experimental Procedures. The advantage of this approach over the other separation techniques that we have employed to study lipid binding of PH domains is that the protein/lipid complex is in equilibrium with a constant concentration of free protein throughout the experiment.

Using this approach, Dyn-PH shows no detectable binding to PI$P_2$-containing vesicles, while PlecN-PH may bind weakly ($K_D \approx 90$ μM), in an interaction that is inhibited by even moderately high concentrations of NaCl. Similarly, PLCδ-PH binds relatively weakly to PIP-containing vesicles (approx 20 μM). The strongest interaction that we could detect by this method was that of PLCδ-PH binding to PI$P_2$-containing vesicles ($K_D = 13$ μM). This interaction was not inhibited by NaCl concentrations that completely inhibited the binding of PlecN-PH to PI$P_2$- or PIP-containing vesicles. Control experiments performed with the SH2 domain of Lck, which elutes from a cation exchanger at an NaCl concentration similar to that required for PlecN-PH showed that it also binds to PI$P_2$- and PIP-containing vesicles at low salt concentrations.

The apparent $K_D$ values quoted above are overestimates of the real $K_D$, since a portion of the loaded lipid was clearly observed to bind to the gel-filtration column. A control experiment with the SH2 domain from Lck showed this also binds to PI$P_2$ and PIP containing vesicles under conditions used (50 mM MOPSA. PH 6.8, 100 mM NaCl), probably through non-specific electrostatic interaction with negatively charged vesicles.

Indeed, Lck-SH2 and each PH domain are basic. They all bind to an SP cation exchange column, eluting at NaCl concentrations of 150 mM (Dyn-PH), 200 mM (PLCδ-PH), 500 mM (Lck-SH2) and 600 mM (PlecN-PH). It might therefore be expected that their non-specific binding to PI$P_2$ containing vesicles will show a similar trend. This appears true for PlecN-PH and Lck-SH2, whereas the observed binding of PLCδ-PH is anomously tight. Evidence presented above shows that this is a specific, high affinity event. Specific binding to PI$P_2$ containing vesicles is therefore not a feature of all PH domains. Of the PH domains studied here, it is observed only with PLCδ-PH. We therefore suggest that the PI$P_2$-binding observed by Harlan, J. E. et al., Nature 371, 168–170, 1994 for PlecN-PH and other PH domains may result from nonspecific electrostatic interactions.

Example 10
Do Inositol Polyphosphates Bind to Other PH Domains?

Since PLCδ-PH binds specifically to a particular inositol polyphosphate, and more weakly to a series of other inositol polyphosphates, we were interested to determine whether Dyn-PH and PlecN-PH would bind to one of the inositol polyphosphates that were available to us. This was motivated in part by reports of, as yet unidentified specific inositol polyphosphate binding proteins in rat brain cytosolic (Kanematsu et al., 1992) and membrane (Theibert, A. B., et al., *J. Biol. Chem.* 267, 9071–9079, 1992) fractions, as well as an I(1345)P$_4$-binding protein in porcine platelets. Cullen, P. J. et al., FEBS Letts. 358, 240–242, 1995.

Neither PlecN-PH nor Dyn-PH showed evidence of binding to I(145)P$_3$ or I(134)P$_3$ in the gel-filtration experiments described above. Furthermore, ITC employing mixtures of inositol polyphosphates showed that no inositol polyphosphate employed in this study binds to Dyn-PH with a K$_D$ value of less than 20 μM. However, when ITC was performed with Dyn-PH at high concentrations (1 mM), we could detect only weak binding of both I(13456)P$_5$ and I(123456)P$_6$. Our estimate for the K$_D$ of in both cases is in the range of 100 μM. It therefore appears that high affinity inositol polyphosphate binding is unlikely to be a general feature of PH domains, although our observations with DynPH, and the report of Harlan, J. E. et al., *Nature* 371, 168–170, 1994 may indicate that other PH domains bind to molecules of a similar nature.

TABLE 1

Titration Calorimetry of Inositol Polyphosphate Binding to PLCδ-PH

| Inositol Phosphate[a] | Concentration in cell (μM) | Stoichiometry n[b] | K$_B$ × 10$^6$ (M$^{-1}$) | K$_D$ (μM) | ΔG" kcal · M$^{-1}$ | ΔH kcal · M$^{-1}$ | ΔS" cal · M$^{-1}$ · K$^{-1}$ |
|---|---|---|---|---|---|---|---|
| I(145)P$_3$ | 11 | 1.00 ± 0.00 | 7.90 ± 0.57 | 0.13 | −9.41 | −19.8 ± 0.1 | −34.3 |
| I(145)P$_3$ | 10.8 | 0.85 ± 0.01 | 2.90 ± 0.40 | 0.34 | −8.82 | −20.9 ± 0.4 | −40.5 |
| I(145)P$_3$ | 20 | 1.02 ± 0.00 | 6.47 ± 0.67 | 0.35 | −9.23 | −18.3 ± 0.2 | −30.4 |
| Mean I(145)P$_3$ | — | 0.96 ± 0.09 | 5.76 ± 2.58 | 0.21 ± 0.12 | −9.15 ± 0.30 | −19.7 ± 1.3 | −35.2 ± 5.1 |
| PIP$_2$[c] | 12 | 0.88 ± 0.02 | 1.05 ± 0.19 | 0.95 | −8.22 | −13.6 ± 0.4 | −18.1 |
| PIP$_2$[c] | 12 | 0.87 ± 0.02 | 0.47 ± 0.05 | 2.12 | −7.74 | −17.4 ± 0.4 | −32.4 |
| PIP$_2$[c] |  |  |  |  |  |  |  |
| Mean PIP$_2$ | — |  |  |  |  |  |  |
| GPIP$_2$ | 30 | 1.08 ± 0.01 | 3.11 ± 0.29 | 0.32 | −8.86 | −13.5 ± 0.1 | −15.6 |
| GPIP$_2$ | 53 | 1.14 ± 0.01 | 2.50 ± 0.31 | 0.40 | −8.72 | −13.2 ± 0.1 |  |
| Mean GPIP$_2$ | — | 1.11 ± 0.04 | 2.80 ± 0.43 | 0.36 ± 0.06 | −8.79 ± 0.10 | −13.4 ± 0.2 | −15.4 ± 0.3 |
| I(13456)P$_5$ | 72 | 0.89 ± 0.00 | 0.39 ± 0.01 | 2.56 | −7.63 | −9.46 ± 0.04 | 6.1 |
| I(13456)P$_5$ | 53 | 0.98 ± 0.01 | 0.33 ± 0.02 | 3.03 | −7.53 | −8.98 ± 0.11 | −4.9 |
| Mean IP$_5$ | — | 0.94 ± 0.06 | 0.36 ± 0.04 | 2.80 ± 0.33 | −7.58 ± 0.07 | −9.22 ± 0.34 | −5.5 ± 0.8 |

[a]All insitol phosphates are D-myo isomers.
[b]Stoichiometries are quoted for IP$_n$ as the ligand.
[c]Stoichiometry and concentration assumes that 50% of the PIP$_2$ in the vesicle preparation (present in the calorimeter cell) is available for binding to PLCδ-PH.

TABLE 2

Specificity of Inositol Phosphate Binding to PLCδ-PH by Competition Assay

| Inositol Polyphosphate | K$_D$ (μM) |
|---|---|
| A. Inositol Mono- and Bis-Phosphates | |
| I-2-P | >60 |
| GPI | >60 |
| D-I(14)P$_2$ | >12 |
| D-I(24)P$_2$ | >12 |
| D-I(45)P$_2$ | >12 |
| B. Inositol Trisphosphates | |
| D-I(145)P$_3$ | 0.2 |
| D-I(245)P$_3$ | 4.7 |
| D-I(134)P$_3$ | >12 |
| LPI(145)P$_3$ | 8.1 |
| GPIP$_2$ | 0.45 |
| C. Inositol Tetra- and Higher Phosphates | |
| D-I(1345)P$_4$ | >2 |
| D-I(3456)P$_4$ | 3.2 |
| D-I(1256)P$_4$ | 12 |
| D-I(1346)P$_4$ | 5.3 |
| D-I(13456)P$_5$ | 4.4 |
| D-I(123456)P$_5$ | 2.9 |
| I(SO$_4$)$_6$ | >60 |

Values for $K_D$ were determined from the ratio of molar excess of competitor to compete the number of counts bound by 50% to that observed for unlabeled $I(145)P_3$. This ratio was then multiplied by 0.2 µM, the $K_D$ determined for $I(145)P_3$ binding to PLCδ-PH by ITC. Values for which a precise number is given represent the mean of at least two experiments.

---

What is claimed is:

1. A method of screening potential agents useful for treatment of a disease or condition having an abnormality in a signal transduction pathway involving an interaction between a pleckstrin homology domain and a pleckstrin homology domain binding partner, comprising:
   (a) selecting said potential agents; and
   (b) assaying said potential agents for those able to disrupt or promote said interaction as an indication of a useful said agent,
   wherein said potential agents are selected from the group consisting of organic and inorganic compounds of molecular weight less than 500.

2. The method of claim 1 wherein said pleckstrin homology domain is part of a phospholipase $C\delta_1$ protein.

3. The method of claim 1 wherein said binding partner is $PIP_2$.

4. The method of claim 1 wherein said binding partner is $I(145)P_3$.

5. The method of claim 1, wherein said disease or condition is a neurological disorder.

6. The method of claim 1, wherein said disease or condition is hypertension.

7. The method of claim 1, wherein said abnormality is characterized by a normal level of interaction between the pleckstrin homology domain and the pleckstrin homology domain binding partner.

8. The method of claim 1, wherein said binding partner is an agonist.

9. The method of claim 1, wherein said binding partner is an antagonist.

10. The method of claim 1, wherein the interaction between a pleckstrin homology domain and a pleckstrin homology domain binding partner is specific.

11. A method of screening potential agents useful for treatment of a disease or condition having an abnormality in a signal transduction pathway involving an interaction between a pleckstrin homology domain and a pleckstrin homology domain binding partner, comprising:

(a) selecting said potential agents; and
(b) assaying said potential agents for those able to disrupt or promote said interaction as an indication of a useful said agent, wherein said potential agent has an $EC_{50}$ or an $IC_{50}$ of less than 5 μM.

12. The method of claim 11, wherein said pleckstrin homology domain is part of a phospholipase $C\delta_1$ protein.

13. The method of claim 11 wherein said binding partner is $PIP_2$.

14. The method of claim 11, wherein said binding partner is $I(145)P_3$.

15. The method of claim 11, wherein said disease or condition is a neurological disorder.

16. The method of claim 11, wherein said disease or condition is hypertension.

17. The method of claim 11, wherein said abnormality is characterized by a normal level of interaction between the pleckstrin homology domain and the pleckstrin homology domain binding partner.

18. The method of claim 11, wherein said binding partner is an agonist.

19. The method of claim 11, wherein said binding partner is an antagonist.

20. The method of claim 11, wherein the interaction between a pleckstrin homology domain and a pleckstrin homology domain binding partner is specific.

* * * * *

SEQUENCE LISTING

<160> NUMBER OF SEQ ID NOS: 4

<210> SEQ ID NO 1
<211> LENGTH: 109
<212> TYPE: PRT
<213> ORGANISM: Homo sapiens
<220> FEATURE:
<223> OTHER INFORMATION: PLC delta 1

<400> SEQUENCE: 1

```
Leu Lys Gly Ser Gln Leu Leu Lys Val Lys Ser Ser Ser Trp Arg Arg
 1               5                  10                  15

Glu Arg Phe Tyr Lys Leu Gln Glu Asp Cys Lys Thr Ile Trp Gln Glu
            20                  25                  30

Ser Arg Lys Val Met Arg Thr Pro Glu Ser Gln Leu Phe Ser Ile Glu
        35                  40                  45

Asp Ile Gln Glu Val Arg Met Gly His Arg Thr Glu Gly Leu Glu Lys
    50                  55                  60

Phe Ala Arg Asp Val Pro Glu Asp Arg Cys Phe Ser Ile Val Phe Lys
65                  70                  75                  80

Asp Gln Arg Asn Thr Leu Asp Ile Ala Pro Ser Pro Ala Asp Ala Gln
                85                  90                  95

His Trp Val Leu Gly Leu His Lys Ile Ile His His Ser
                100                 105
```

<210> SEQ ID NO 2
<211> LENGTH: 105
<212> TYPE: PRT
<213> ORGANISM: Homo sapiens
<220> FEATURE:
<223> OTHER INFORMATION: Dynamin

<400> SEQUENCE: 2

```
Arg Lys Gly Trp Leu Thr Ile Asn Asn Ile Gly Ile Met Lys Gly Gly
 1               5                  10                  15

Ser Lys Glu Tyr Trp Phe Val Leu Thr Ala Glu Asn Leu Ser Trp Tyr
            20                  25                  30

Lys Asp Asp Glu Glu Lys Glu Lys Lys Tyr Met Leu Ser Val Asp Asn
        35                  40                  45

Leu Lys Leu Arg Asp Val Glu Lys Gly Phe Met Ser Ser Lys His Ile
    50                  55                  60

Phe Ala Leu Phe Asn Thr Glu Gln Arg Asn Val Tyr Lys Asp Tyr Arg
65                  70                  75                  80

Gln Leu Glu Ala Cys Glu Thr Gln Glu Glu Val Asp Ser Trp Lys Ala
                85                  90                  95

Ser Phe Leu Arg Ala Gly Val Tyr Pro
                100                 105
```

<210> SEQ ID NO 3
<211> LENGTH: 105

```
<212> TYPE: PRT
<213> ORGANISM: Homo sapiens
<220> FEATURE:
<223> OTHER INFORMATION: Spectrin

<400> SEQUENCE: 3

Met Glu Gly Phe Leu Asn Arg Lys His Glu Trp Glu Ala His Asn Lys
 1               5                  10                  15

Lys Ala Ser Ser Arg Ser Trp His Asn Val Tyr Cys Val Ile Asn Asn
                20                  25                  30

Gln Glu Met Gly Phe Tyr Lys Asp Ala Lys Ser Ala Ala Ser Gly Ile
             35                  40                  45

Pro Tyr His Ser Glu Val Pro Val Ser Leu Lys Glu Ala Ile Cys Glu
         50                  55                  60

Val Ala Leu Asp Tyr Lys Lys Lys His Val Phe Lys Leu Arg Leu
 65                  70                  75                  80

Ser Asp Gly Asn Glu Tyr Leu Gln Ala Lys Asp Asp Glu Glu Met Asn
                 85                  90                  95

Thr Trp Ile Gln Ala Ile Ser Ser Ala
                100                 105

<210> SEQ ID NO 4
<211> LENGTH: 96
<212> TYPE: PRT
<213> ORGANISM: Homo sapiens
<220> FEATURE:
<223> OTHER INFORMATION: Pleckstrin N

<400> SEQUENCE: 4

Arg Glu Gly Tyr Leu Val Lys Lys Gly Ser Val Phe Asn Thr Trp Lys
 1               5                  10                  15

Pro Met Trp Val Val Leu Leu Glu Asp Gly Ile Glu Phe Tyr Lys Lys
                20                  25                  30

Lys Ser Asp Asn Ser Pro Lys Gly Met Ile Pro Leu Lys Gly Ser Thr
             35                  40                  45

Leu Thr Ser Pro Cys Gln Asp Phe Gly Lys Arg Met Phe Val Phe Lys
     50                  55                  60

Ile Thr Thr Thr Lys Gln Gln Asp His Phe Gln Ala Ala Phe Leu Glu
 65                  70                  75                  80

Glu Arg Asp Ala Trp Val Arg Asp Ile Asn Lys Ala Ile Lys Cys Ile
                85                  90                  95
```